US006946812B1

(12) United States Patent
Martin et al.

(10) Patent No.: US 6,946,812 B1
(45) Date of Patent: Sep. 20, 2005

(54) METHOD AND APPARATUS FOR PROVIDING FORCE FEEDBACK USING MULTIPLE GROUNDED ACTUATORS

(75) Inventors: Kenneth M. Martin, Palo Alto, CA (US); Mike D. Levin, Sunnyvale, CA (US); Louis B. Rosenberg, Pleasanton, CA (US)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 09/106,565

(22) Filed: Jun. 29, 1998

Related U.S. Application Data

(63) Continuation of application No. 08/736,161, filed on Oct. 25, 1996, now Pat. No. 5,828,197.

(51) Int. Cl.[7] .............................................. G05B 19/10
(52) U.S. Cl. ............. 318/567; 318/568.16; 318/568.23; 318/569; 318/560; 318/600; 901/46
(58) Field of Search ........................... 318/567, 568.16, 318/568.22, 569, 560, 600; 901/46; 364/413.02

(56) References Cited

U.S. PATENT DOCUMENTS

| 2,906,179 A | 9/1959 | Bower |
| 2,972,140 A | 2/1961 | Hirsch |
| 2,996,822 A | 8/1961 | Souza |
| 3,157,853 A | 11/1964 | Hirsch |
| 3,220,121 A | 11/1965 | Cutler |

(Continued)

FOREIGN PATENT DOCUMENTS

| EP | 0 349 086 A1 | 1/1990 |
| JP | H2-185278 | 7/1990 |
| JP | H4-8381 | 1/1992 |
| JP | H5-192449 | 8/1993 |
| JP | H7-24147 | 1/1995 |

(Continued)

OTHER PUBLICATIONS

Burdea et al., "Dextous telerobotics with force feedback—an overview. Part 1: Human factors", Rutgers—The State University of New Jersey, Dept. of Electrical and Computer Engineering, Piscataway, NJ, Jun. 22, 1990.

Hannaford et al., "Performance Evaluation of a Six–Axis Generalized Force–Reflecting Teleoperator," IEEE Transactions on Systems, Man, and Cybernetics, vol. 21, 3, 1991 IEEE.

(Continued)

*Primary Examiner*—Karen Masih

(57) ABSTRACT

An apparatus and method for interfacing the motion of a user-manipulable object with a computer system includes a user object physically contacted or grasped by a user. A 3-D spatial mechanism is coupled to the user object, such as a stylus or a medical instrument, and provides three degrees of freedom to the user object. Three grounded actuators provide forces in the three degrees of freedom. Two of the degrees of freedom are a planar workspace provided by a closed-loop linkage of members, and the third degree of freedom is rotation of the planar workspace provided by a rotatable carriage. Capstan drive mechanisms transmit forces between actuators and the user object and include drums coupled to the carriage, pulleys coupled to-grounded actuators, and flexible cables transmitting force between the pulleys and the drums. The flexibility of the cable allows the drums to rotate with the carriage while the pulleys and actuators remain fixed to ground. The interface also may include a floating gimbal mechanism coupling the linkage to the user object. The floating gimbal mechanism includes rotatably coupled gimbal members that provide three degrees of freedom to the user object and capstan mechanisms coupled between sensors and the gimbal members for providing enhanced sensor resolution.

37 Claims, 11 Drawing Sheets

U.S. PATENT DOCUMENTS

| | | |
|---|---|---|
| 3,490,059 A | 1/1970 | Paulsen et al. ............... 73/133 |
| 3,497,668 A | 2/1970 | Hirsch |
| 3,517,446 A | 6/1970 | Corlyon et al. |
| 3,623,064 A | 11/1971 | Kagan |
| 3,795,150 A | 3/1974 | Eckhardt ...................... 74/5.4 |
| 3,875,488 A | 4/1975 | Crocker et al. ............. 318/648 |
| 3,902,687 A | 9/1975 | Hightower |
| 3,903,614 A | 9/1975 | Diamond et al. |
| 3,911,416 A | 10/1975 | Feder |
| 3,919,691 A | 11/1975 | Noll ....................... 340/172.5 |
| 3,942,147 A | 3/1976 | Josephson |
| 3,944,798 A | 3/1976 | Eaton ...................... 235/151.3 |
| 3,988,845 A | 11/1976 | Boatman |
| 4,023,290 A | 5/1977 | Josephson |
| 4,101,884 A | 7/1978 | Benton, Jr. |
| 4,127,752 A | 11/1978 | Lowthorp |
| 4,160,508 A | 7/1979 | Frosch et al. |
| 4,216,467 A | 8/1980 | Colston .................. 340/365 L |
| 4,232,724 A | 11/1980 | Brown |
| 4,236,325 A | 12/1980 | Hall et al. |
| 4,242,823 A | 1/1981 | Bruno |
| 4,262,549 A | 4/1981 | Schwellenbach |
| 4,333,070 A | 6/1982 | Barnes |
| 4,436,188 A | 3/1984 | Jones ........................ 188/378 |
| 4,438,605 A | 3/1984 | DeLucia |
| 4,448,083 A | 5/1984 | Hayashi ................... 73/862.04 |
| 4,464,117 A | 8/1984 | Foerst |
| 4,477,043 A | 10/1984 | Repperger .................. 244/223 |
| 4,484,191 A | 11/1984 | Vavra |
| 4,513,235 A | 4/1985 | Acklam et al. |
| 4,550,617 A | 11/1985 | Fraignier et al. ........ 73/862.04 |
| 4,571,834 A | 2/1986 | Fraser et al. ................ 33/1 PT |
| 4,581,491 A | 4/1986 | Boothroyd |
| 4,593,470 A | 6/1986 | Davies ...................... 33/1 CC |
| 4,599,070 A | 7/1986 | Hladky et al. |
| 4,638,798 A | 1/1987 | Shelden et al. ......... 128/303 B |
| 4,653,011 A | 3/1987 | Iwano ....................... 364/513 |
| 4,676,002 A | 6/1987 | Slocum .................... 33/1 MP |
| 4,679,331 A | 7/1987 | Koontz ........................ 33/551 |
| 4,688,983 A | 8/1987 | Lindbom ................... 414/735 |
| 4,694,533 A | 9/1987 | Doyen |
| 4,703,443 A | 10/1987 | Moriyasu .................... 364/559 |
| 4,708,656 A | 11/1987 | de Vries et al. |
| 4,713,007 A | 12/1987 | Alban |
| 4,750,487 A | 6/1988 | Zanetti ................... 128/303 B |
| 4,775,289 A | 10/1988 | Kazerooni ................. 414/735 |
| 4,791,934 A | 12/1988 | Brunnett ..................... 128/653 |
| 4,794,392 A | 12/1988 | Selinko |
| 4,800,721 A | 1/1989 | Cemenska et al. ............. 60/393 |
| 4,803,413 A | 2/1989 | Kendig et al. ............. 318/648 |
| 4,811,608 A | 3/1989 | Hilton ..................... 73/862.04 |
| 4,885,565 A | 12/1989 | Embach |
| 4,888,877 A | 12/1989 | Enderle et al. ................ 33/559 |
| 4,891,764 A | 1/1990 | McIntosh |
| 4,891,889 A | 1/1990 | Tomelleri .................... 33/503 |
| 4,907,970 A | 3/1990 | Meenen, Jr. ................. 434/45 |
| 4,907,973 A | 3/1990 | Hon ........................... 434/262 |
| 4,930,770 A | 6/1990 | Baker |
| 4,934,694 A | 6/1990 | McIntosh |
| 4,961,267 A | 10/1990 | Herzog ....................... 33/503 |
| 4,962,448 A | 10/1990 | DeMaio et al. ............. 364/146 |
| 4,982,504 A | 1/1991 | Soderberg et al. ........... 33/502 |
| 5,002,727 A | 3/1991 | Okimoto et al. |
| 5,005,306 A | 4/1991 | Kinstler |
| 5,007,300 A | 4/1991 | Siva ..................... 74/471 XY |
| 5,019,761 A | 5/1991 | Kraft |
| 5,022,384 A | 6/1991 | Freels |
| 5,022,407 A | 6/1991 | Horch et al. |
| 5,035,242 A | 7/1991 | Franklin et al. |
| 5,038,089 A | 8/1991 | Szakaly |
| 5,050,608 A | 9/1991 | Watanabe et al. ........ 128/653 R |
| 5,078,152 A | 1/1992 | Bond et al. |
| 5,103,404 A | 4/1992 | McIntosh ............... 318/568.22 |
| 5,116,051 A | 5/1992 | Moncricf et al. ........ 273/448 B |
| 5,142,931 A | 9/1992 | Menahem .............. 74/471 XY |
| 5,143,505 A | 9/1992 | Burdea et al. .................. 414/5 |
| 5,146,566 A | 9/1992 | Hollis, Jr. et al. .......... 395/275 |
| 5,148,377 A | 9/1992 | McDonald ................. 364/560 |
| 5,156,363 A | 10/1992 | Cizewski et al. ............ 244/223 |
| 5,165,897 A | 11/1992 | Johnson |
| 5,175,459 A | 12/1992 | Danial et al. |
| 5,184,306 A | 2/1993 | Erdman et al. ........ 364/474.05 |
| 5,184,319 A | 2/1993 | Kramer ...................... 364/806 |
| 5,185,561 A | 2/1993 | Good et al. ................. 318/432 |
| 5,186,695 A | 2/1993 | Mangseth et al. |
| 5,187,874 A | 2/1993 | Takahashi et al. ............. 33/502 |
| 5,189,806 A | 3/1993 | McMurtry et al. ............ 33/503 |
| 5,193,963 A | 3/1993 | McAffee et al. ................ 414/5 |
| 5,212,473 A | 5/1993 | Louis |
| 5,220,260 A | 6/1993 | Schuler ...................... 318/561 |
| 5,223,776 A | 6/1993 | Radke et al. ............. 318/568.1 |
| 5,228,356 A | 7/1993 | Chuang ................. 74/471 XY |
| 5,230,623 A | 7/1993 | Guthrie et al. ................. 433/72 |
| 5,235,868 A | 8/1993 | Culver ....................... 74/471 |
| 5,240,417 A | 8/1993 | Smithson et al. |
| 5,243,266 A | 9/1993 | Kasagami et al. ........ 318/568.1 |
| 5,251,127 A | 10/1993 | Raab ..................... 364/413.13 |
| 5,259,120 A | 11/1993 | Chapman et al. ............. 33/502 |
| 5,261,174 A | 11/1993 | Blegen |
| 5,271,290 A | 12/1993 | Fischer |
| 5,275,174 A | 1/1994 | Cook |
| 5,283,970 A | 2/1994 | Aigner |
| 5,289,273 A | 2/1994 | Lang .......................... 348/121 |
| 5,296,846 A | 3/1994 | Ledley ....................... 345/161 |
| 5,297,057 A | 3/1994 | Kramer et al. |
| 5,299,810 A | 4/1994 | Pierce et al. |
| 5,309,140 A | 5/1994 | Everett, Jr. et al. |
| 5,334,027 A | 8/1994 | Wherlock |
| 5,379,663 A | 1/1995 | Hara ..................... 74/471 XY |
| 5,389,865 A | 2/1995 | Jacobus et al. ......... 318/568.11 |
| 5,397,323 A | 3/1995 | Taylor et al. ............... 606/130 |
| 5,402,582 A | 4/1995 | Raab ........................... 33/503 |
| 5,405,152 A | 4/1995 | Katanics et al. ............. 273/438 |
| 5,412,880 A | 5/1995 | Raab ........................... 33/503 |
| 5,414,337 A | 5/1995 | Schuler ...................... 318/561 |
| 5,436,542 A | 7/1995 | Petelin et al. ............... 318/567 |
| 5,436,622 A | 7/1995 | Gutman et al. |
| 5,437,607 A | 8/1995 | Taylor |
| 5,445,166 A | 8/1995 | Taylor ........................ 128/897 |
| 5,459,382 A | 10/1995 | Jacobus et al. ......... 318/568.11 |
| 5,466,213 A | 11/1995 | Hogan et al. |
| 5,491,477 A | 2/1996 | Clark et al. .................... 341/20 |
| 5,512,919 A | 4/1996 | Araki ......................... 345/156 |
| 5,547,382 A | 8/1996 | Yamasaki et al. |
| 5,575,761 A | 11/1996 | Hajianpour |
| 5,576,727 A | 11/1996 | Rosenberg et al. .......... 345/179 |
| 5,587,937 A | 12/1996 | Massie et al. ............... 364/578 |
| 5,623,582 A | 4/1997 | Rosenberg ..................... 395/99 |
| 5,625,576 A | 4/1997 | Massie et al. ............... 364/578 |
| 5,629,594 A | 5/1997 | Jacobus et al. ......... 318/568.11 |
| 5,642,469 A | 6/1997 | Hannaford et al. ............ 395/99 |
| 5,690,582 A | 11/1997 | Ulrich et al. |
| 5,691,898 A | 11/1997 | Rosenberg et al. .......... 364/190 |
| 5,709,219 A | 1/1998 | Chen et al. .................. 128/782 |
| 5,721,566 A | 2/1998 | Rosenberg et al. .......... 345/161 |
| 5,731,804 A | 3/1998 | Rosenberg .................. 345/156 |
| 5,734,373 A | 3/1998 | Rosenberg et al. .......... 345/161 |
| 5,742,278 A | 4/1998 | Chen et al. .................. 345/156 |
| 5,753,834 A * | 5/1998 | Stewart ...................... 73/865.3 |
| 5,754,023 A | 5/1998 | Roston et al. ............... 318/561 |
| 5,766,016 A | 6/1998 | Sinclair et al. |

| | | | |
|---|---|---|---|
| 5,767,839 A | * | 6/1998 | Rosenberg .................. 345/161 |
| 5,769,640 A | | 6/1998 | Jacobus et al. ............. 434/262 |
| 5,785,630 A | | 7/1998 | Bobick et al. |
| 5,790,108 A | | 8/1998 | Salcudean et al. .......... 345/184 |
| 5,802,353 A | | 9/1998 | Avila et al. ................. 395/500 |
| 5,805,140 A | | 9/1998 | Rosenberg et al. ......... 345/161 |
| 5,844,392 A | | 12/1998 | Peurach et al. ........ 318/568.17 |
| 5,872,438 A | | 2/1999 | Roston .................. 318/568.11 |
| 5,889,670 A | | 3/1999 | Schuler et al. .............. 364/186 |
| 6,111,577 A | | 8/2000 | Zilles et al. |
| 6,160,489 A | | 12/2000 | Perry et al. |
| 6,422,941 B1 | | 7/2002 | Thorner et al. |

FOREIGN PATENT DOCUMENTS

| | | |
|---|---|---|
| WO | WO9426167 | 11/1994 |
| WO | WO9502233 | 1/1995 |
| WO | WO9502801 | 1/1995 |
| WO | WO9520787 | 8/1995 |
| WO | WO9520788 | 8/1995 |
| WO | WO9532459 | 11/1995 |
| WO | WO9616397 | 5/1996 |
| WO | WO9622591 | 7/1996 |

OTHER PUBLICATIONS

Ellis, et al., "Design and Evaluation of a High–Performance Prototype Planar Haptic Interface", DSC–vol. 49, Advances in Robotics, Mechatronics, and Haptic Interfaces ASME 1993.

Hasser, "Tactile Feedback for a Force–Reflecting Haptic Display", University of Dayton, Dayton, Ohio, Decemer 1995.

Adelstein, et al., "Design and Implementation of a Force Reflecting Manipulandum for Manual Control Research", NASA–Ames Research Center, Moffett Field, CA , 1992.

Iwata, "Volume Haptization", Institute of Engineering Mechanics, University of Tsukuba, Tsukuba, Japan, IEEE 1993.

Howe, "Task Performance with a Dextrous Teleoperated Hand System", Harvard University, Division of Applied Sciences, Cambridge, MA 02138, Presented at Telemanipulator Technology 32, Proceedings of SPIE, Vol 1833, 1992.

Snow et al., "Compact Force–Reflecting Hand Controller", Jet Propulsion Laboratory, California Institute of Technology, Pasadena, CA 1991.

McAffee, "Teleoperator Subsystem/Telerobot Demonstrator: Force Reflecting Hand Controller Equipment Manual", Jet Propulsion Laboratory, California Institute of Technology, 1988.

Schmult, "Application Areas for a Force–Feedback Joystick", DSC–Vol 49, Advances in Robotics, Mechatronics, and Haptic Interfaces, ASME 1993.

Winey III, "Computer Simulated Visual and Tactile Feedback as an Aid to Manipulator and Vehicle control", Massachuetts Institute of Technology, 1981.

Russo, "The Design and Implementation of a Three Degree–of–Frredom Force Output Joystick", Department of Mechanical Engineering, 1990.

Hiroo Iwata, "Pen–based Haptic Virtual Environment", Institute of Engineering Mechanics, University of Tsukuba, Tsukuba, Japan.

J.N. Herndon, "The State–of–the–Art Model M–2 Maintenance System", Proc. of the 1984 Natinal Topical Meeting on Robotics and Remote Handling in Hostile Environment, American Nuclear Society, pp. 147–154.

Minsky, et al., "Feeling and Seeing: Issues in Force Display", Dept. of Computer Science, University of North Carolina at Chapel Hill, Chapel Hill, NC 27599, ACM 1990.

Batter, et al., "Grope–1: A Computer Display to the Sense of Feel", University of North Carolina at Chapel Hill, Chapel Hill, North Carolina, USA.

Gotow, et al., "Perception of Mechanical Properties at the Man–Machine Interface", Dept. of Mechanical Engineering and The Robotics Institute, Carnegie Mellon University, Pittsburg, PA 15213.

Atkinson, et al., "Computing with Feeling", University of California, San Diego, Department of Chemistry, 1976.

A. Michael Noll, "Man–Machine Tactile Communication", Polytechnic Institute of Brooklyn, 1971.

Ming Ouh–Young, "Force Display in Molecular Docking", University of North Carolina at Chapel Hill, 1990.

Meyer, et al., "A Survey of Position Trackers", University of North Carolina, Presence, vol. 1, No. 2, Spring 1992.

Immersion PROBE–MD, "High Performance Model of the Immersion Probe:", Immersion Corporation, P.O. Box 8669, Palo Alto, CA 94309–8669.

Geoffrey Smith, "Call It Palpable Progress", Science & Technology, Business Week, Oct. 9, 1995, p. 93.

D.S. Tavkhelidze, et al., "Kinematic Analysis of Five–Link Spherical Mechanisms", Mechanism and Machine Theory, Pergamon Press, 1974, vol. 9, pp. 181–190.

S.C. Jacobsen, et al., "High Performance, High Dexterity, Force Reflective Teleoperator II", ANS Topical Meeting on Robotics and Remote Systems, Albuquerque, New Mexico, Feb. 24–27, 1991.

Buttolo, et al., "Pen–Based Force Display for Precision Manipulation in Virtual Environments", Biorobotics Laboratory, Dept. of Electrical Engineering, Univ. of Washington, Seattle, Proc. IEEE Virtual Reality Annual International Symposium, Mar., 1995, pp. 217–224.

Immersion Corp., "The Personal Digitizer", High Performance Digitizing for Your Desktop.

Fischer, et al., "Specification and Design of Input Devices for Teleoperation", Robotics Research Group, Dept. of Engineering Science, Univ. of Oxford, KV Siva, Engineering Science Division, AEA Technology, Harwell UK.

Young, et al., "Force Display Performs Better Than Visual Display in a Simple 6–D Docking Task", Computer Science Department, University of North Carolina at Chapel Hill, IEEE 1989.

Bejczy, et al., "The Phantom Robot: Predictive Displays for Teleoperation with Time Delay", JPL, California Institute of Technology, IEEE 1990.

Kotoku, "A Predictive Display with Force Feedback and its Application to Remote Manipulation System with Transmission Time Delay," 1992 IEEE/RSJ Int'l Conf. on Intelligent Robots and Systems, Raleigh, NC, Jul. 7–10, 1992.

Kilpatrick, Paul Jerome, "The Use of a Kinesthetic Supplement in an Interactive Graphics System", Xerox University Microfilms, Ann Arbor, Michigan, 1976.

Kelley, A. et al., "MagicMouse: Tactile and Kinesthetic Feedback in the Human–Computer Interface using and Electromagnetically Actuated Input/Output Device," Dept. of Electrical Engineering, Univ. of British Columbia, 1993, pp. 1–27.

Salcudean, S.E., "A Six Degree–of–Freedom, Hydraulic, One Person Motion Simulator," Dept. of Electrical Engineering, Univ. of British Columbia, 1993.

Hayward, V. et al., "Design and Multi–Objective Optimization of a Linkage for a Haptic Interface," Advances in Robot Kinematics and Computationed Geometry, Kluwer Academic Publishers, 1994, pp. 359–368.

Millman, P. et al., "Design of a Four Degree–of–Freedom Force–Reflecting Manipulandum with a Specified Force/Torque Workspace," Proc. of 1991 IEEE Int'l Conf. on Robotics and Automation, IEEE 1991, pp. 1488–1492.

Brooks Jr., F., "Project GROPE—Haptic Displays for Scientific Visualization," Computer Graphics, vol. 24, No. 4, 1990, pp. 177–185.

Hannaford, B. et al., "Force–Feedback Cursor Control," NASA Tech Brief, vol. 13, No. 11, Item #21, 1989, pp. 1–4.

Rosenberg, "Virtual Fixtures: Perceptual Overlays Enhance Operator Performance in Telepresence Tasks," Ph.D. Dissertation, Stanford University, Jun. 1994.

Wiker, "Teletouch Display Development: Phase 1 Report," *Technical Report 1230*, Naval Ocean Systems Center, San Diego, Jul. 1988.

Yamakita et al., "Tele–Virtual Reality of Dynamic Mechanical Model," *Proceedings of the 1992 IEEE/RSJ International Conference on Intelligent Robots and Systems*, Raleigh, NC, Jul. 7–10, 1992.

Aukstakalnis et al., "Silicon Mirage: The Art and Science of Virtual Reality," ISBN 0–938151–82–7, pp. 129–180, 1992.

Bliss, "Optical–to–Tactile Image Conversion for the Blind," IEEE Transactions on Man–Machine Systems, vol. MMS–11, No. 1, pp. 58–65, Mar. 1970.

Calder, "Design of A Force–Feedback Touch–Introducing Actuator For Teleoperator Robot Control," Bachelor of Science Thesis, MIT, Jun. 23, 1983.

"Cyberman Technical Specification," Logitech Cyberman SWIFT Supplement, Apr. 5, 1994.

Eberhardt et al., "Inducing Dynamic Haptic Perception by The Hand: System Description and Some Results," DSC–vol. 55–1, Dynamic Systems and Control: vol. 1, ASME 1994, pp. 345–351.

Gobel et al., "Tactile Feedback Applied to Computer Mice," International Journal of Human–Computer Interaction, vol. 7, No. 1, pp. 1–24, 1995.

Johnson, "Shape–Memory Alloy Tactile Feedback Actuator," Armstrong Aerospace Medical Research Laboratory, AAMRL–TR–90–039, Aug., 1990.

Kaczmarek et al., "Tactile Displays," Virtual Environment Technologies, pp. 349–414.

Kontarinis et al., "Tactile Display of Vibratory Information in Teleoperation and Virtual Environments," PRESENCE, vol. 4, No. 4, pp. 387–402, 1995.

Lake, "Cyberman from Logitech," GameBytes, 1994.

Noll, "Man–Machine Tactile," SID Journal, Jul./Aug. 1972 Issue.

Ouhyoung et al., "The Development of A Low–Cost Force Feedback Joystick and its Use in the Virtual Reality Environment," Proceedings of the Third Pacific Conference on Computer Graphics and Applications, Pacific Graphics '95, Seoul, Korea, Aug. 21–24, 1995, pp. 309–319.

Pimentel et al., "Virtual Reality: through the new looking glass," $2^{nd}$ Edition; McGraw–Hill, ISBN 0–07–050167–X, pp. 41–202, 1994.

Patrick, "Design, Construction, and Testing of Fingertip Tactile Display for Interaction with Virtual and Remote Environments," Master of Science Thesis, MIT, Nov. 8, 1990.

Adelstein, "A Virtual Environment System For The Study of Human Arm Tremor," *Ph.D. Dissertation*, Dept. of Mechanical Engineering, MIT, Jun. 1989, archived Mar. 13, 1990.

Bejczy, "Sensors, Controls, and Man–Machine Interface for Advanced Teleoperation," *Science*, vol. 208, No. 4450, pp. 1327–1335, 1980.

Bejczy et al., "Generalization of Bilateral Force–Reflecting Control of Manipulators," *Proceedings Of Fourth CISM–IFToMM*, Sep. 8–12, 1981.

McAffee et al., "Teleoperator Subsystem/Telerobot Demonstrator: Force Reflecting Hand Controller Equipment Manual," *JPL* 1988, JPL D–5172.

Minsky, "Computational Haptics: The Sandpaper System for Synthesizing Texture for a Force–Feedback Display," *Ph.D. Dissertation*, MIT, Jun. 1995, archived Jul. 6, 1995.

Jacobsen et al., "High Performance, Dextrous Telerobotic Manipulator With Force Reflection," *Intervention/ROV '91 Conference & Exposition*, Hollywood, Florida, May 21–23, 1991.

Shimoga, "Finger Force and Touch Feedback Issues in Dexterous Telemanipulation," *Proceedings of Fourth Annual Conference on Intelligent Robotic Systems for Space Exploration*, Rensselaer Polytechnic Institute, Sep. 30–Oct. 1, 1992.

IBM Technical Disclosure Bulletin, "Mouse Ball–Actuating Device With Force and Tactile Feedback," vol. 32, No. 9B, Feb. 1990.

Terry et al., "Tactile Feedback In A Computer Mouse," *Proceedings of Fourteenth Annual Northeast Bioengineering Conference, University of New Hampshire*, Mar. 10–11, 1988.

Howe, "A Force–Reflecting Teleoperated Hand System for the Study of Tactile Sensing in Precision Manipulation," *Proceedings of the 1992 IEEE International Conference on Robotics and Automation*, Nice, France, May 1992.

Eberhardt et al., "OMAR—A Haptic display for speech perception by deaf and deaf–blind individuals," *IEEE Virtual Reality Annual International Symposium*, Seattle, WA, Sep. 18–22, 1993.

Rabinowitz et al., "Multidimensional tactile displays: Identification of vibratory intensity, frequency, and contractor area," *Journal of The Acoustical Society of America*, vol. 82, No. 4, Oct. 1987.

Bejczy et al., "Kinesthetic Coupling Between Operator and Remote Manipulator," *International Computer Technology Conference, The American Society of Mechanical Engineers*, San Francisco, CA, Aug. 12–15, 1980.

Bejczy et al., "A Laboratory Breadboard System For Dual–Arm Teleoperation," *SOAR '89 Workshop, JSC*, Houston, TX, Jul. 25–27, 1989.

Ouhyoung et al., "A Low–Cost Force Feedback Joystick and Its Use in PC Video Games," *IEEE Transactions on Consumer Electronics*, vol. 41, No. 3, Aug. 1995.

Marcus, "Touch Feedback in Surgery," *Proceedings of Virtual Reality and Medicine The Cutting Edge*, Sep. 8–11, 1994.

Bejczy, et al., "Universal Computer Control System (UCCS) For Space Telerobots," CH2413–3/87/0000/0318501.00 1987 IEEE, 1987.

Scannell, "Taking a Joystick Ride," Computer Currents, Boston Edition, vol. 9, No. 11, Nov. 1994.

"Component Maintenance Manual With Illustrated Parts List, Coaxial Control Shaker Part No. C–25502," Safe Flight Instrument Corporation, Revised Jan. 28, 2002 (3 pages).

"Technical Manual Overhaul Instructions With Parts Breakdown, Coaxial Control Shaker Part No. C–25502," Safe Flight Instrument Corporation, Revised Jul. 15, 1980 (23 pages).

Baigrie, "Electric Control Loading—A Low Cost, High Performance Alternative," *Proceedings of Interservice/Industry Training Systems Conference*, pp. 247–254, Nov. 6–8, 1990.

Iwata, "Pen–based Haptic Virtual Environment," 0–7803–1363–1/93 IEEE, pp. 287–292, 1993.

Russo, "The Design and Implementation of a Three Degree of Freedom Force Output Joystick," *MIT Libraries Archives* pp. 1–131, May 1990, archived Aug. 14, 1990.

Brooks et al., "Hand Controllers for Teleoperation—A State–of–the–Art Technology Survey and Evaluation," *JPL Publication 85–11*, NASA–CR–175890; N85–28559, pp. 1–84, Mar. 1, 1985.

Jones et al., "A perceptual analysis of stiffness," ISSN 0014–4819 Springer International (Springer–Verlag); *Experimental Brain Research*, vol. 79, No. 1, pp. 150–156, 1990.

Burdea et al., "Distributed Virtual Force Feedback, Lecture Notes for Workshop on Force Display in Virtual Environments and its Application to Robotic Teleoperation," *1993 IEEE International Conference on Robotics and Automation*, pp. 25–44, May 2, 1993.

Snow et al., Model–X Force–Reflecting–Hand–Controller, NT Control No. NP0–17851; JPL Case No. 7348, pp. 1–4 with 45 pages of attachments, Jun. 15, 1989.

Ouh–Young, "Force Display in Molecular Docking," Doctoral Dissertation, University of North Carolina at Chapel Hill, UMI Order No. 9034744, p. 1–369, 1990.

Tadros, "Control System Design for a Three Degree of Freedom Virtual Environment Simulator Using Motor/Brake Pair Actuators," *MIT Archive*, pp. 1–88, Feb. 1990, archived Aug. 13, 1990.

Caldwell et al., "Enhanced Tactile Feedback (Tele–Taction) Using a Multi–Functional Sensory System," 1050–4729/93, pp. 955–960, 1993.

Adelstein et al., "Design and Implementation of a Force Reflecting Manipulandum for Manual Control research," DSC–vol. 42, *Advances in Robotics*, pp. 1–12, 1992.

Gotow et al., "Controlled Impedance Test Apparatus for Studying Human Interpretation of Kinesthetic Feedback," WA11–11:00, pp. 332–337.

Stanley et al., "Computer Simulation of Interacting Dynamic Mechanical Systems Using Distributed Memory Parallel Processors," DSC–vol. 42, *Advances in Robotics*, pp. 55–61, ASME 1992.

Russo, "Controlling Dissipative Magnetic Particle Brakes in Force Reflective Devices," DSC–vol. 42, *Advances in Robotics*, pp. 63–70, ASME 1992.

Kontarinis et al., "Display of High–Frequency Tactile Information to Teleoperators," *Telemanipulator Technology and Space Telerobotics*, Won S. Kim, Editor, Proc. SPIE vol. 2057, pp. 40–50, Sep. 7–9, 1993.

Patrick et al., "Design and Testing of A Non–reactive, Fingertip, Tactile Display for Interaction with Remote Environments," *Cooperative Intelligent Robotics in Space*, Rui J. deFigueiredo et al, Editor, Proc. SPIE vol. 1387, pp. 215–222, 1990.

* cited by examiner

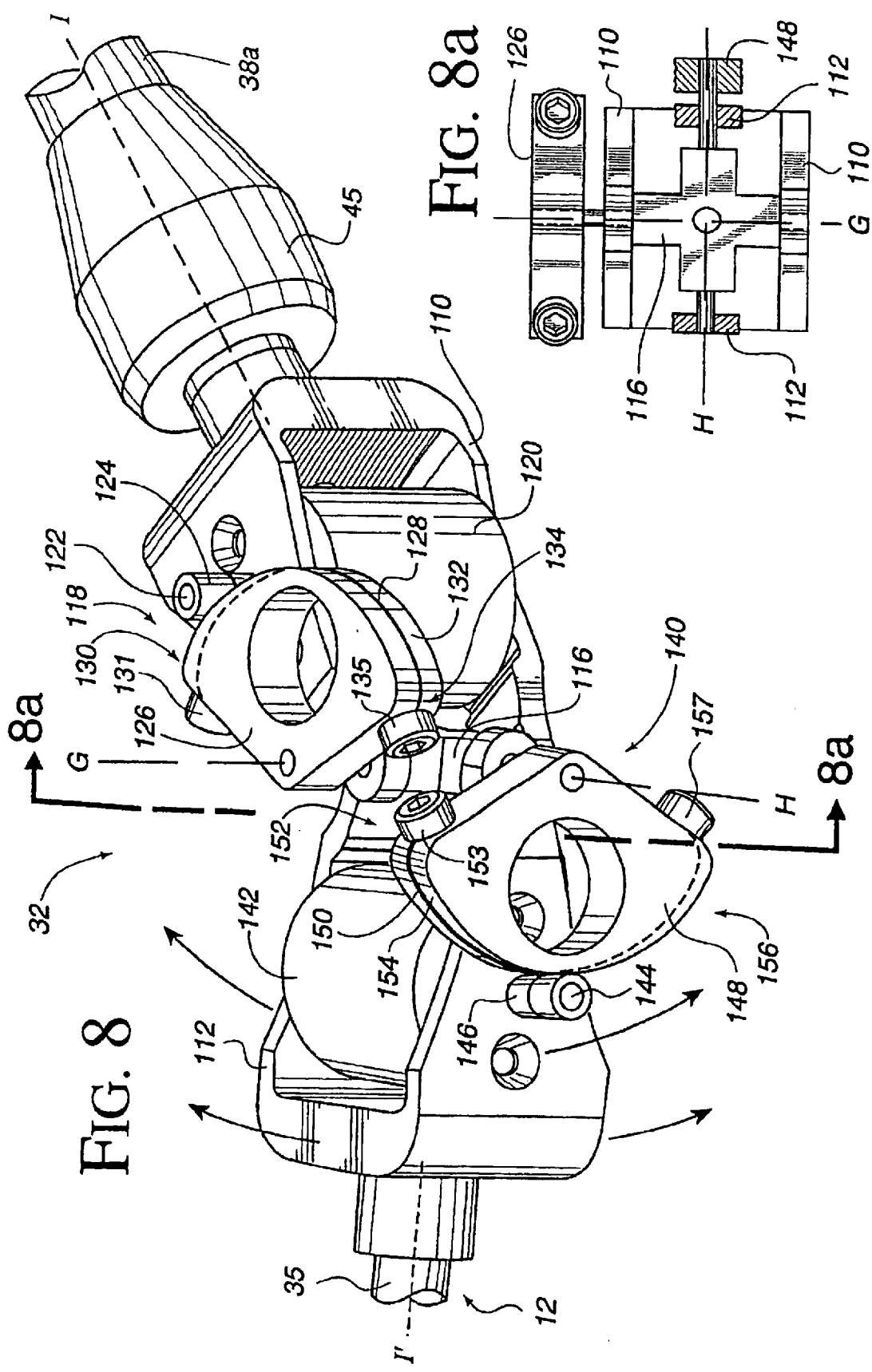

METHOD AND APPARATUS FOR PROVIDING FORCE FEEDBACK USING MULTIPLE GROUNDED ACTUATORS

This application is a continuation of Ser. No. 08/736,161 filing date Oct. 25, 1996 now U.S. Pat. No. 5,828,197.

BACKGROUND OF THE INVENTION

The present invention relates generally to interface devices between humans and computers, and more particularly to computer interface devices that provide force feedback to the user.

Virtual reality computer systems provide users with the illusion that they are part of a "virtual" environment. A virtual reality system will typically include a computer processor, such as a personal computer or workstation, specialized virtual reality software, and virtual reality I/O devices such as head mounted displays, sensor gloves, three dimensional ("3D") pointers, etc.

Virtual reality computer systems can be used for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. For example, a virtual reality computer system can allow a doctor-trainee or other human operator or user to "manipulate" a scalpel or probe within a computer-simulated "body", and thereby perform medical procedures on a virtual patient. In this instance, the I/O device which is typically a 3D pointer, stylus, or the like is used to represent a surgical instrument such as a scalpel or probe. As the "scalpel" or "probe" moves within a provided space or structure, results of such movement are updated and displayed in a body image displayed on the screen of the computer system so that the operator can gain the experience of performing such a procedure without practicing on an actual human being or a cadaver. In other applications, virtual reality computer systems allow a user to manipulate the controls of complicated and expensive vehicles and machinery for training and/or entertainment purposes. For example, a pilot or astronaut in training can operate a fighter aircraft or spacecraft by manipulating controls such as a control joystick and buttons and view the results of controlling the aircraft on a virtual reality simulation of the aircraft in flight. In yet other applications, a user can manipulate objects and tools in the real world, such as a stylus, and view the results of the manipulation in a virtual reality world with a "virtual stylus" viewed on a screen, in 3-D goggles, etc.

For virtual reality systems to provide a realistic (and therefore effective) experience for the user, sensory feedback and manual interaction should be as natural as possible. Therefore, in addition to sensing and tracking a user's manual activity and feeding such information to the controlling computer to provide a 3D visual representation to the user, a human interface mechanism should also provide force feedback ("haptic" or tactile sensations) to the user. The need for the user to experience realistic force information and sensation is extensive in many kinds of simulation and other applications. For example, in medical/surgical simulations, the "feel" of a probe or scalpel simulator is important as the probe is moved within the simulated body. It would invaluable to a medical trainee to learn through force feedaback how an instrument moves within a body, how much force is required depending on the operation performed, the space available in a body to manipulate an instrument, etc. In simulations of vehicles or equipment, force feedback for controls such as a joystick can be necessary to realistically teach a user the force required to move the joystick when steering in specific situations, such as in a high acceleration environment of an aircraft. In virtual world simulations where the user can manipulate objects, force feedback is necessary to realistically simulate physical objects; for example, if a user touches a pen to a table, the user should feel the impact of the pen on the table. An effective human/computer interface not only acts as an input device for tracking motion, but also as an output device for producing realistic force sensations. A "high bandwidth" interface system, which is an interface that mechanically and electrically allows accurate control over force feedback using fast control signals within a broad range of frequencies, is therefore desirable in these and other applications.

In addition, there is a desire to provide force feedback to users of computer systems in the entertainment industry. Styluses, joysticks, and other interface devices can be used to provide force feedback to a user playing a video game or experiencing a simulation for entertainment or learning purposes. Through such an interface device, a computer system can convey to the user the physical sensation of colliding into a wall, moving through a liquid, driving over a bumpy road, and other sensations. The user can thus experience an entire sensory dimension in the gaming experience that was previously absent. Force feedback interfaces can provide a whole new modality for human-computer interaction.

There are number of devices that are commercially available for interfacing a human with a computer for virtual reality simulations. There are, for example, 2-dimensional input devices such as mice, trackballs, joysticks, and digitizing tablets, as wells as 3-dimensional interface devices. A 3-dimensional human/computer interface tool sold under the trademark Immersion Probe™ is marketed by Immersion Human Interface Corporation of Santa Clara, Calif., and allows manual control in 3-dimensional virtual reality computer environments. A pen-like stylus allows for dexterous 3-dimensional manipulation in six degrees of freedom using a serail configuration of links and joints. The Immersion Probe, however, does not provide force feedback to a user and thus does not allow a user to experience an entire sensory dimension in virtual reality simulations. Prior art force feedback instruments and joysticks provide physical sensations to the user by controlling motors that are coupled to the joystick.

In typical multi-degree of freedom apparatuses that include force feedback, there are several disadvantages. Since actuators which supply force feedback tend to be heavier and larger than sensors, they would provide inertial constraints if added to a device such as the Immersion Probe. In a typical force feedback device, such as Per Force from Cybernet Systems Inc., a serial chain of links and actuators is implemented to achieve multiple degrees of freedom in a desired object positioned at the end of the chain, i.e., each actuator is coupled to the previous actuator. The user who manipulates the object must carry the inertia of all of the subsequent actuators and links except for the first actuator in the chain; which is grounded. For example, the user carries the weight of five ungrounded motors in the Per Force device. Other force feedback devices have a different, non-serial type of linkage, but include several ungrounded motors; for example, the Phantom from Sensable Devices Inc., includes three driven degrees of freedom but only one out of three motors is grounded. The end result is high inertia which corrupts the bandwidth of the system, providing the user with an inaccurate interface. These interfaces also introduce tactile "noise" to the user through friction and compliance in signal transmission and limit the degree of sensitivity conveyed to the user through the actuators of the device.

Other systems, such as a joystick using a slotted bail mechanism, are able to provide two grounded actuators, which enhances the realism of the force feedback experienced by the user. However, these systems are limited in bandwidth by their mechanisms, which tend to be inaccurate and ill-suited for effectively transmitting forces to the user. In other other force feedback interfaces, such as the Impulse Engine from Immersion Corporation, two grounded actuators provide high bandwidth force feedback to a user in two degrees of freedom. However, if it is desired to provide forces in a third degree of freedom, then the user is typically required to carry the weight of the third actuator supplying force in that third degree of freedom, which degrades the realism of the forces felt using the force feedback interface device.

In yet other force feedback interface systems, motors are coupled to a mechanism using cables which transmit forces from the motor to the mechanism. However, in many of these interface systems, the forces from one motor influence the tension on other motors and cables in the system, thus causing additional degradation in the force transmission. In addition, the calculation of forces to provide a desired force sensation to the user can be complicated in such a coupled actuator system, thus decreasing the response time of the system.

SUMMARY OF THE INVENTION

The present invention provides a human/computer interface apparatus and method which can provide from one to six degrees of freedom to a user-manipulable object and highly realistic force feedback to the user of the apparatus. The structure of the apparatus and a capstan drive permits actuators to be grounded and thus positioned such that their inertial contribution to the system is very low.

An interface apparatus and method of the present invention for interfacing the motion of a user-manipulable object with a computer system includes a user manipulable object physically contacted by a user, such as a stylus, medical/surgical instrument, joystick, or other graspable object. A 3-D spatial mechanism is coupled to the user object and provides at least three degrees of freedom to the user object, where the spatial mechanism includes multiple members including a ground member coupled to ground. Three actuators are rigidly coupled to the ground member and together apply a three-dimensional force to the user manipulable object in response to actuator signals from the computer system. Each actuator does not carry the weight of any of the other actuators, thus providing a highly accurate and realistic 3-D interface for the user. A sensor for detecting a position of said user manipulable object along said degree of freedom and outputting sensor signals to said computer system. A sensor detects a position of the user object along the degree of freedom and outputs sensor signals to the electrical system.

The spatial mechanism preferably includes a planar five-member closed loop linkage riding on a rotatable carriage. The five-member linkage provides two degrees of freedom to the user manipulable object and includes two base members, two central members, and a ground member. The rotatable carriage is coupled to the ground member and provides a third degree of freedom to the user manipulable object. Force is transmitted from each said actuators to the spatial mechanism using capstan drive mechanisms. Two of the capstan drive mechanisms each include a drum coupled to the carriage such that a member of the spatial mechanism is coupled to the drum, and a pulley coupled to a grounded actuator. A drum is coupled to a corresponding pulley by a cable or other flexible member so that the actuator is operative to rotate the pulley and transmit force to the spatial mechanism in the first two degrees of freedom with no substantial backlash. Since the drums are coupled to the carriage, the pulley is coupled to the grounded actuator, and the cable between them is flexible, the drums may be rotated with the carriage while the pulleys remain fixed in position and the cable twists, thus providing a third degree of freedom for the user object. A third capstan drive mechanism is also preferably coupled between the the carriage and the grounded third actuator to provide forces in the third degree of freedom. Thus, all three actuators are grounded and decoupled in force from each other, thereby avoiding the inertia created by the weight of the actuators being carried by other actuators or carried by the user.

An interface apparatus of the present invention also may include a floating gimbal mechanism coupling one of the members of a linkage or other mechanism to the user manipulatable object. The floating gimbal mechanism includes a plurality of rotatably coupled gimbal members that provide two rotary degrees of freedom to the user manipulable object. A sensor is provided for each of the gimbal members for measuring a position of the members relative to each other in one of the rotary degrees of freedom. Preferably, a capstan mechanism is coupled between each of the sensors and one of the gimbal members, where each capstan mechanism includes a capstan drum rotatable about an axis of one of the rotary degrees of freedom and a pulley coupled to the sensor and coupled to the drum by a flexible member, such as a metal cable. The capstan mechanisms provide mechanical reduction and thus enhance the resolution of the sensors. In other embodiments, the user manipulable object is rotatable about a longitudinal axis of the object to provide an additional degree of freedom for the object.

The interface apparatus of the present invention includes three grounded, decoupled actuators to provide forces in three degrees of freedom of a user manipulable object. This improvement allows the user to manipulate the object free from the inertia caused by the weight of the actuators, and allows the other actuators to transmit forces to the user object without having to compensate for the inertia of other actuators, thereby providing more accurate and realistic forces. These unique twist capstan drive mechanisms allow the three actuators to be grounded while also providing mechanical advantage for the high bandwidth and low backlash forces from the actuators. The floating gimbal mechanism of the present invention provides capstan mechanisms in a unique configuration that allows the sensing resolution of the floating gimbal sensors to be enhanced while minimizing the weight of the floating gimbal mechanism. These improvements allow a computer system to have more complete and accurate control over a low-cost interface providing realistic force feedback.

These and other advantages of the present invention will become apparent to those skilled in the art upon a reading of the following specification of the invention and a study of the several figures of the drawing.

BRIEF DESCRIPTION OF THE DRAWINGS

FIG. 8 is a perspective view of the floating gimbal mechanism used in the mechanical apparatus of FIG. 2 for fourth and fifth degrees of freedom;

FIG. 8a is a cross sectional view of FIG. 8 along line 8a—8a showing the intermediate member of the floating gimbal mechanism;

DETAILED DESCRIPTION OF PREFERRED EMBODIMENTS

Figure 1:
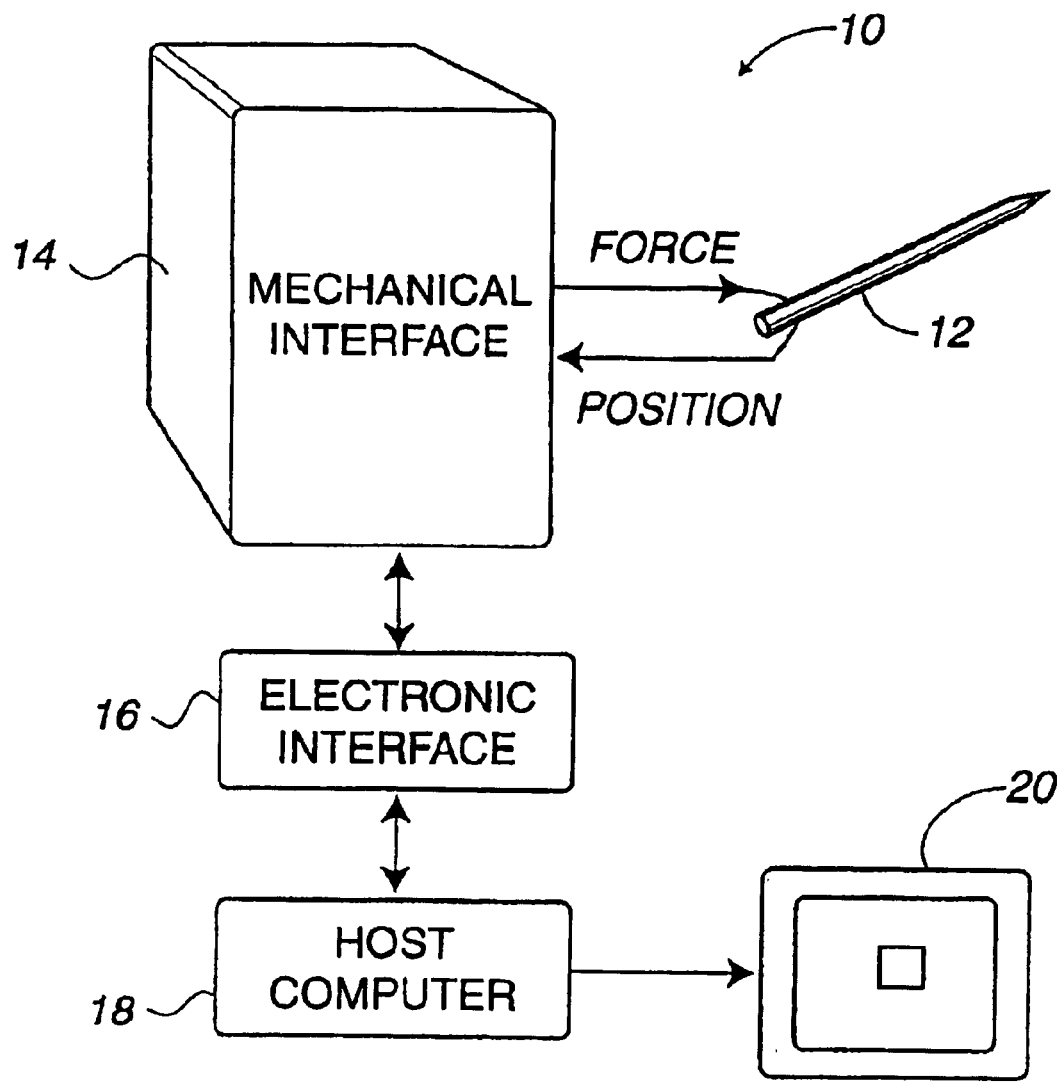
FIG. 1 is a perspective view of a virtual reality system which employs a mechanical interface apparatus of the present invention to interface a user manipulable object with a computer system.

FIG. 1 illustrates a force feedback virtual reality system 10 used to provide a user-manipulable object in a virtual environment, simulation, or video game. Virtual reality system 10 includes a user manipulable object 12, a mechanical interface 14, an electronic interface 16, and a host computer 18. The illustrated virtual reality system 10 includes a stylus 12 as a user manipulable object.

User manipulable 12 used in conjunction with the present invention is manipulated by a user and, for example, virtual reality images are displayed on a display screen 20 of the computer system 18 in response to such manipulations. For example, a user can move a stylus 12 to correspondingly move a computer generated object, such as a cursor or other image, in a virtual environment. The available degrees of freedom in which user manipulable object 12 can be moved are determined from the mechanical interface 14, described below.

It will be appreciated that a great number of other types of user manipulable objects can be used with the method and apparatus of the present invention. In fact, the present invention can be used with any mechanical object where it is desirable to provide a human/computer interface with multiple degrees of freedom. Such objects may include styluses, medical instruments such as laparoscopes, catheters, endoscopic surgical tools, catheters, hypodermic needles, wires, fiber optic bundles, joysticks, spherical or other shaped hand grips, screw drivers, steering wheels/controls, pool cues, etc. Some of these other objects, such as a medical instrument, are described in detail subsequently.

Mechanical interface apparatus 14 interfaces mechanical input and output between the user manipulating object 12 and host computer 18 implementing the simulation or game environment. Mechanical interface 14 provides multiple degrees of freedom to object 12; in the preferred embodiment, at least three and up to six degrees of freedom are provided to the user manipulable object, although fewer degrees of freedom can be provided in alternate embodiments.

The user manipulates object 12 in 3-D space and the position and/or orientation of object 12 is translated using mechanical interface 14 into a form suitable for interpretation by sensors of the mechanical interface 14, as described in greater detail below. The sensors track the movement of the object 12 in three-dimensional space and provide suitable elentronic signals to electronic interface 16. Electronic interface 16, in turn, provides position and/or orientation information to host computer 18. In addition, host computer 18 and/or electronic interface 16 provides force feedback information to actuators coupled to mechanical interface 14, and the actuators generate forces on members of the mechanical apparatus to provide forces on object 12 in provided or desired degrees of freedom. The user experiences the forces generated on the stylus as realistic simulations of force sensations such as jolts, textures, "barrier" forces, and the like. For example, when a surface is generated on computer screen 20 and a computer object controlled by the user collides with the surface, the computer 18 will send force feedback signals to the electrical interface 16 and mechanical apparatus 14 to generate collision forces on a stylus 12. Mechanical interface 14 is shown in greater detail with respect to FIG. 2.

Electronic interface 16 is a component of the virtual reality system 10 and may couple the mechanical apparatus 14 to the host computer 18. Electronic interface 16 can be included within a housing of mechanical apparatus 14 or portions of the electronic interface can be provided as a separate unit with its own housing. Alternatively, electronic interface 16 can be included in host computer 18. More particularly, electronic interface 16 includes sensor and actuator interfaces that convert electrical signals to appropriate forms usable by mechanical apparatus 14 and host computer 18. One suitable embodiment of interface 16 is described in detail with reference to FIG. 9, in which the interface can include a dedicated interface card to be plugged into computer 16. In alternate embodiments, interface 16 can include a microprocessor local to the mechanical interface 14 and separate from any microprocessors in the host computer 18 to control "reflex" force feedback independently of the host computer, as described below.

The electronic interface 16 can be coupled to mechanical interface apparatus 14 by a bus 15 (or may be included within the housing of apparatus 14) and is coupled to the computer 18 by a bus (or may be directly connected to the computer using a interface card). In other embodiments, signals can be sent to and from interface 16 and computer 18 by wireless transmission/reception. In preferred embodiments of the present invention, the interface 16 serves as an input/output (I/O) device for the computer 18. The interface 16 can also receive inputs from other input devices or controls that are associated with mechanical interface 14 or object 12 and can relay those inputs to computer 18. For example, commands sent by the user activating a button on mechanical interface 14 can be relayed to computer 18 to implement a command or cause the computer 18 to output a command to the mechanical apparatus 14. Such input devices are described in greater detail with respect to FIG. 9.

Host computer 18 is preferably a personal computer or workstation, such as an IBM-PC compatible computer or Macintosh personal computer, or a SUN or Silicon Graphics workstation. For example, the computer 18 can operate under the Windows™ or MS-DOS operating system in conformance with an IBM PC AT standard. Alternatively, host computer system 18 can be one of a variety of home video game systems commonly connected to a television set, such as systems available from Nintendo, Sega, or Sony. In other embodiments, home computer system 18 can be a "set top box" which can be used, for example, to provide interactive television functions to users, or a "hollow" or "internet" computer which allows users to interact with a local or global network using standard connections and protocols such as used for the Internet and World Wide Web. Host computer preferably includes a host microprocessor, random access memory (RAM), read only memory (ROM), input/output (I/O) circuitry, and other components of computers well-known to those skilled in the art.

Host computer 18 implements a host application program with which a user is interacting via mechanical interface apparatus 14 and other peripherals, if appropriate. For example, the host application program can be a medical simulation, video game, scientific analysis program, or other application program that utilizes input of user object 12 and outputs force feedback to the object 12. The host application program checks for input signals received from electronic interface 16 and sensors of mechanical interface 14, and outputs force values and commands to be converted into forces on user object 12. Suitable software drivers which interface such simulation software with computer input/output (I/O) devices are available from Immersion Human Interface Corporation of San Jose, Calif.

Display device 20 is can be included in host computer 18 and can be a standard display screen or CRT, 3-D goggles, or any other visual interface. Typically, the host application provides images to be displayed on display device 20 and/or other feedback, such as auditory signals. For example, display screen 20 can display images from a game application program. Images describing a moving, first person point of view can be displayed, as in a virtual reality game. Or, images describing a third-person perspective of objects, backgrounds, etc. can be displayed. Alternatively, images froma simulation, such as a medical simulation, can be displayed, e.g., images of tissue and a representation of object 12 moving through the tissue, etc.

Figure 2:
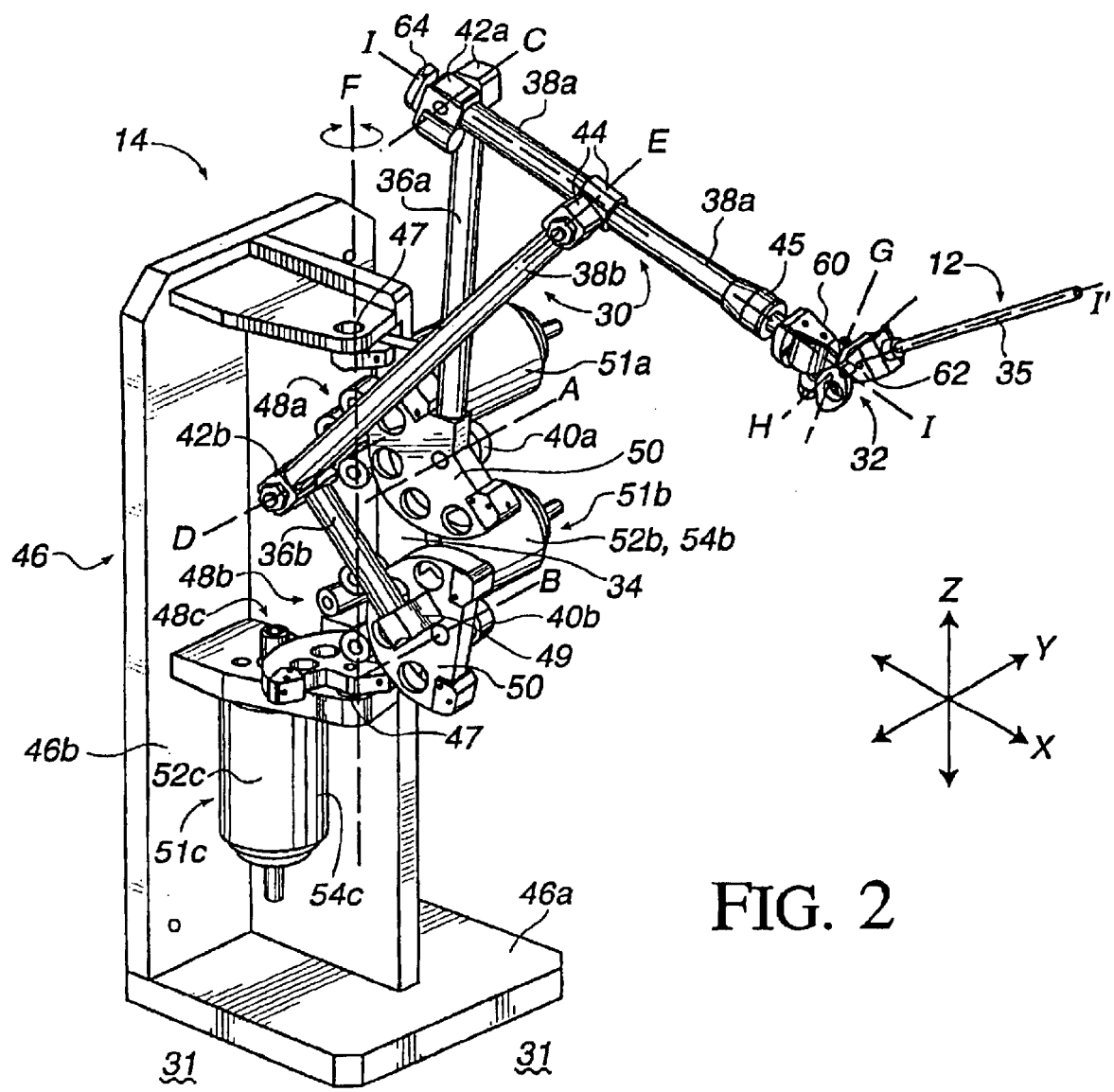
FIG. 2 is a perspective view of a mechanical interface apparatus of the present invention for providing mechanical input and output to a computer system and having a stylus object.
Figure 3:
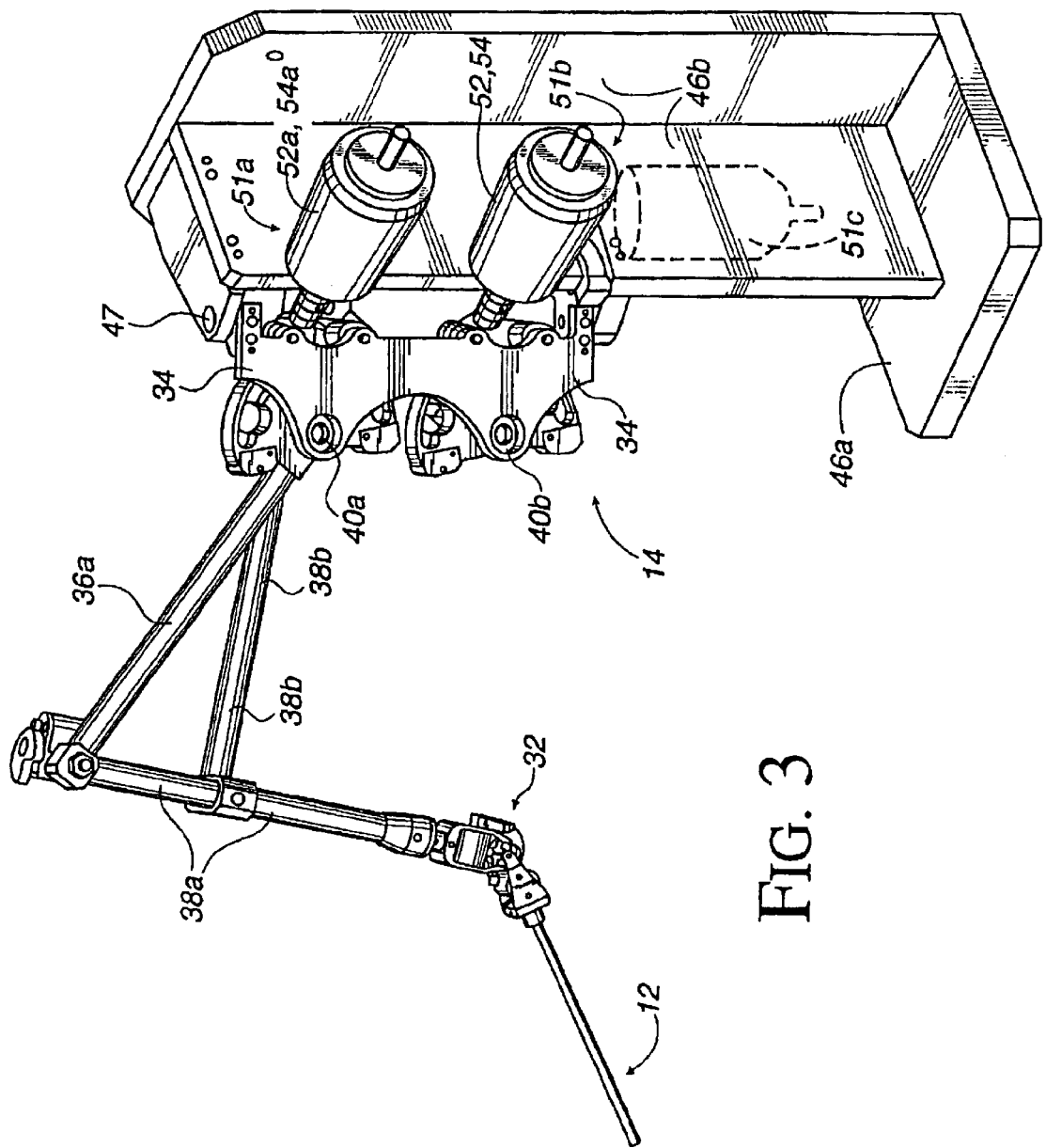
FIG. 3 is a different perspective view of the mechanical apparatus of FIG. 2.

In FIG. 2, a perspective view of mechanical interface apparatus 14 for providing mechanical input and output in accordance with the present invention is shown. FIG. 3 shows a perspective view of the mechanical apparatus 14 from a different perspective to illustrate the configuration and operation of apparatus 14. Apparatus 14 includes a mechanical linkage 30, a ground member 46, and a floating gimbal mechanism 32. In the embodiment of FIGS. 2 and 3, user manipulatable object 12 is preferably a stylus 35 or stylus-like object coupled to gimbal mechanism 32.

Mechanical linkage 30 provides support for object 12 and couples the object to a ground member on a grounded surface 31, such as a tabletop or other support. Linkage 30 is, in the described embodiment, a 5-member (or "5-bar") linkage including rotatable carriage 34 that acts as a local ground, base member 36a coupled to a carriage 34, central member 38a coupled to base member 36a, base member 36b coupled to carriage 34, and central member 38b coupled to base member 36b. Fewer or greater numbers of members in the linkage can be provided in alternate embodiments. Herein, linkage 30 is part of a 3-D spatial mechanism that includes linkage 30 and ground member 46 (described below).

Rotatable carriage 34 acts as a local ground member for linkage 30, i.e., the carriage 34 is coupled to ground with respect to the linkage 30. However, carriage 34 can also rotate independently of ground 31 and a ground member 46 to which the carriage is coupled, as described below, and is thus not grounded with respect to the entire 3-D spatial mechanism. The members of linkage 30 are rotatably coupled to one another through the use of rotatable bearings or pivots, wherein base member 36a is rotatably coupled to carriage 34 by bearing 40a and can rotate about an axis A (a capstan drive mechanism is coupled between the base member and the bearing, as discussed below). Central member 38a is rotatably coupled to base member 36a by bearing 42a and can rotate about a floating axis C, base member 36b is rotatably coupled to carriage 34 by bearing 40b and can rotate about axis B, central member 38b is rotatably coupled to base member 36b by bearing 42b and can rotate about floating axis D, and central member 38b is rotatably coupled to central member 38b by bearing 44 such that central member 38b and central member 38a may rotate relative to each other about floating axis E. In the described embodiment, central member 38b is coupled at its end to a mid-portion of central member 38a and object 12 is coupled to the end of central member 38a. Floating gimbal mechanism 32 is coupled to member 38a by bearing 45. In an alternate embodiment, the end of central member 38b can be coupled to the end of member 38a, as in a parallel linkage disclosed in U.S. Pat. No. 6,028,593 by Rosenberg et al., hereby incorporated by reference in its entirety.

The axes C, D, and E are "floating" in the sense that they are not fixed in one position relative to ground surface 31 as are axes A and B. Preferably, the axes C, D, and E are all substantially parallel to each other. In alternate embodiments, base members 36a and 36b can be coupled to ground member 34 at the same axis, so that axes A and B are provided as one axis about which both members rotate.

Linkage 30 is formed as a five-member closed-loop chain. Each member in the chain is coupled to two other members of the chain. The five-member linkage is arranged such that the members can rotate about their respective axes to provide user object 12 with two degrees of freedom. These provided degrees of freedom are within the x-z plane roughly indicated by the position of members, e.g., the linkage 30 of FIG. 2 allows stylus 12 to be moved within a planar workspace defined by the x-z plane, which is defined by the x- and z-axes as shown in FIG. 2. Linkage 30 is thus a "planar" five-member linkage, since it allows the user object 12 to be moved within a plane. So that the sub-linkage of members 36a and 38a does not interfere with or contact the sub-linkage of members 36b and 38b during movement of the linkage, members 36b and 38b are positioned to one side (i.e., offset along the y-axis) of members 36a and 38a using support 49. Linkage 30 can thus also be referred to as a "parallel link mechanism" since the linkage 30 is not a serial chain of linked members and since members 36a and 38a are movable in a plane substantially parallel to members 36b and 38b.

User object 12 can also be moved in a third degree of freedom. Rotatable carriage 34 (more clearly shown with reference to FIG. 3) acts as a local ground to linkage 30, but also may be rotated independently of linkage 30 with respect to a ground member 46. Ground member 46 is coupled to or resting on a ground surface 31 which provides stability for apparatus 14. Ground member 46 is shown in the embodiment of FIG. 2 having multiple components, including a base 46a supported by ground 31, and a vertical portion 46b to which carriage 34 is coupled.

Figure 4:
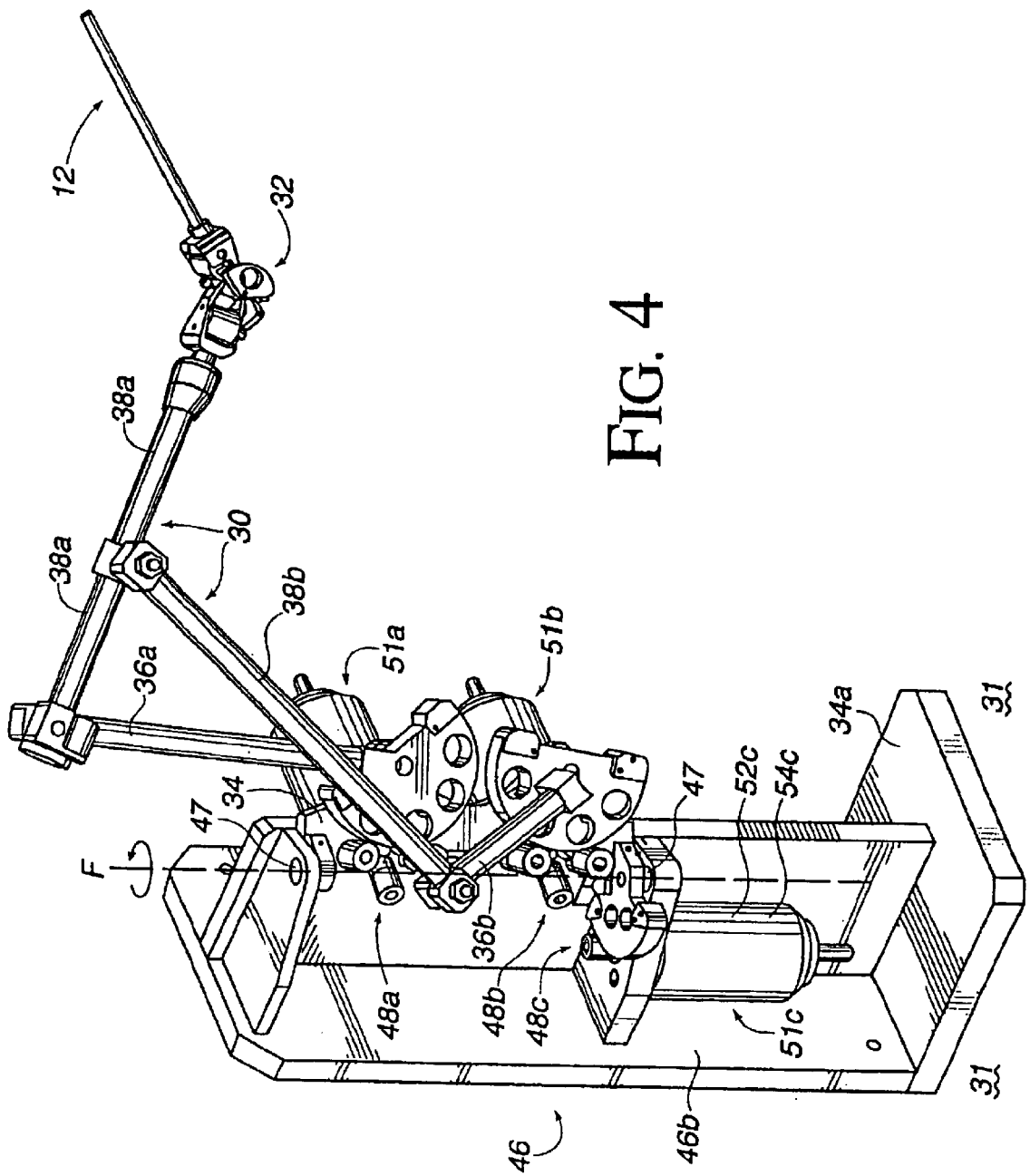
FIG. 4 is a perspective of the mechanical apparatus of FIG. 2 where the user manipulatable object has been moved in a third degree of freedom.

Carriage 34 is rotatably coupled to ground member 46 by two couplings 47 arranged along a linear axis F, thus allowing carriage 34 to rotate about axis F. Base members 36a and 36b are rotatably coupled to carriage 34 such that the base members can rotate about axes A and B, as described previously. Axis F is preferably substantially perpendicular to axis A and axis B. With the inclusion of carriage 34 as a rotatable member, user object 12 can be moved in a third degree of freedom about axis F, thus allowing movement having a component along the y-axis. The motion in the third degree of freedom is illustrated in FIG. 4, where carriage 34, linkage 30, and stylus 12 have been moved counterclockwise about axis F (viewed from above) as compared with the position shown in FIG. 2. Thus, the three degrees of freedom provided to the user object by the spatial mechanism can be described as a planar workspace that is rotatable about an axis F. Carriage 34 carries the drums of the capstan drive mechanisms 48a and 48b about axis F, as described in greater detail with respect to FIG. 6.

Capstan drive mechanisms 48 are provided to transmit forces and motion between electromechanical transducers 51 and the stylus 12. The capstan drive mechanisms each include a drum, a pulley, and a cable. A capstan drive mechanism 48a is preferably coupled between ground member 46 and base member 36a, is routed through carriage 34, and operates to apply a force about axis A with respect to ground to base member 36a. A second capstan drive mechanism 48b is preferably coupled between ground member 34 and base member 36b, is routed through carriage 34, and operates to apply a force about axis B with respect to ground to base member 36b. Capstan mechanisms 48a and 48b include a drum 50 rotatably coupled to carriage 34 to rotate about axes A and B, respectively, and rigidly coupled to base members 36a and 36b, respectively. The capstan mechanisms 48a and 48b also include a number of pulleys coupled to carriage 34 and ground member 46, as described below. In addition, a third capstan drive mechanism 48c is preferably coupled between ground member 46 and carriage 34. Drum 50 of capstan mechanism 48c is rotatably coupled to ground member 34 and is rigidly coupled to carriage 46, thus allowing rotation of carriage 46 about axis F. The capstan drive mechanisms 48a–c are described in greater detail with respect to FIGS. 6 and 7.

Capstan drive mechanisms 48a–c are included in mechanical apparatus 14 for a number of reasons. One is that the structure of the capstan drives 48 allows the actuators of the present invention to all be grounded and allow highly accurate transmission of forces. The capstan mechanisms allow forces with respect to ground to be independently applied to the base members of linkage 30 while allowing the entire linkage 30 to rotate about axis F with respect to ground, as explained below. Another reason for the capstan mechanisms is to provide mechanical advantage for forces generated by the actuators without introducing friction and backlash to the system.

Also coupled to linkage 30 are transducers 51, which may include a sensor and/or an actuators. Transducers 51 are provided between members of the apparatus and provide input to and output between mechanical apparatus 14 and a computer system, such as computer 18.

In the described embodiment, three transducers 51 are preferably bi-directional transducers which include sensors 52. The sensors 52 collectively sense the rotational position/movement of the stylus 12 in the provided degrees of freedom. Sensor 52a senses movement of base member 36a about axis A, sensor 52b senses movement of base member 36b about axis B, and sensor 52c senses movement/position of carriage 46 about axis F. These positions about axes A, B and F, if known, allow the determination of the position of object 12 using known constants such as the lengths of the members of linkage 30 and floating gimbal mechanism 32, and using well-known coordinate transformations.

Sensors 52 can be, for example, relative optical encoders which provide signals to measure the angular rotation (i.e., rotational position) of a shaft of the transducer. The electrical outputs of the encoders are routed to electronic interface 16, as detailed with reference to FIG. 9. Other types of sensors 52 can also be used, such as potentiometers, etc. In addition, it is also possible to use non-contact sensors at different positions relative to mechanical apparatus 14. For example, a Polhemus (magnetic) sensor can detect magnetic fields from objects; or, an optical sensor such as lateral effect photo diode includes an emitter/detector pair that detects positions of the emitter with respect to the detector in one or more degrees of freedom; for example, a photo diode by Hamamatsu Co., part S1743, can be used. These types of sensors are able to detect the position of object 12 in particular degrees of freedom without having to be coupled to a joint of the mechanical apparatus. Alternatively, sensors can be positioned at other locations of relative motion or joints of mechanical apparatus 14. In addition, velocity sensors (e.g., tachometers) and acceleration sensors (e.g., accelerometers) can also be used instead of or in addition to position sensors.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system 10 power-up wherein the sensor's shaft is placed in a known position within the mechanism 14 and a calibration signal is provided to the system to provide the reference position mentioned above. All angles provided by the sensors are thereafter relative to that reference position. Such calibration methods are well known to those skilled in the art and, therefore, will not be discussed in any great detail herein.

Transducers 51 also preferably include actuators 54 to transmit 3-dimensional forces to object 12 in 3-D space, i.e., in three degrees of freedom to the user object. The housing of the transducer of actuator 54a is rigidly coupled to ground member 46 and the actuator transmits rotational forces to base member 36a about axis A through a capstan drive mechanism (described below). Likewise, actuator 54b is rigidly coupled to ground member 46 and transmits rotational forces to base member 36b about axis B through a second capstan drive mechanism. The combination of rotational forces about axis A and axis B allows forces to be transmitted to object 12 in all directions in the planar workspace provided by linkage 30 through the rotational interaction of the members of linkage 30. A third actuator 54c is rigidly coupled to ground member 46 and transmits rotational forces about axis F to carriage 34 through a third capstan drive mechanism, described with reference to FIG. 7. The third actuator provides forces in the third degree of freedom to user manipulable object 12 about axis F. The housings of the three grounded actuators are coupled to the same ground such that the housings of these actuators cannot move with respect to each other.

Actuators 54 can be of two types: active actuators and passive actuators. Active actuators include linear current control motors, stepper motors, pneumatic/hydraulic active actuators, and other types of actuators that transmit a force to force or move an object. For example, active actuators can drive a rotational shaft about an axis in a rotary degree of freedom, or drive a linear shaft along a linear degree of freedom. Active transducers of the present invention are preferably bi-directional, meaning they can selectively transmit force along either direction of a degree of freedom. For example, DC servo motors can receive force control signals to control the direction and torque (force output) that is produced on a shaft. In the described embodiment, active linear current control motors, such as DC servo motors, are used. The control signals for the motor are produced by computer 18 and electronic interface 16 and are detailed with respect to FIG. 9. The motors may include brakes which allow the rotation of the shaft to be halted in a short span of time. The sensors and actuators in transducers 51 are preferably included together as sensor/actuator pair transducers, but can also be provided separately. A suitable transducer for the present invention including both an optical encoder and current controlled motor is a 20 W basket wound servo motor manufactured by Maxon.

In alternate embodiments, other types of active motors can also be used, such as a stepper motor, brushless DC motors, pneumatic/hydraulic actuators, a torquer (motor with limited angular range), or a voice coil, which are well known to those skilled in the actuator art. Stepper motors and the like are not as well suited for the present invention because stepper motor control involves the use of steps or pulses which can be felt as pulsations by the user, thus corrupting the virtual simulation. The present invention is better suited to the use of linear current controlled actuators, which do not have this noise.

Passive actuators can also be used in transducers 51. Magnetic particle brakes, friction brakes, or pneumatic/hydraulic passive actuators can be used in addition to or instead of a motor to generate a damping resistance or friction in a degree of motion. An alternate preferred embodiment only including passive actuators may not be as realistic as an embodiment including motors; however, the passive actuators are typically safer for a user since the user cannot be "jolted" by generated forces. Passive actuators typically can only provide bi-directional resistance to a degree of motion. A suitable magnetic particle brake for interface mechanism 14 is available from Force Limited, Inc. of Santa Monica, Calif.

In other embodiments, all or some of transducers 51 can include only sensors to provide an apparatus without force feedback along designated degrees of freedom. Similarly, all or some of transducers 51 can be implemented as actuators without sensors to provide only force feedback.

In addition, in some embodiments, passive (or "viscous") damper elements can be provided on the bearings of apparatus 14 to remove energy from the system and intentionally increase the dynamic stability of the mechanical system. This may have the side effect of degrading the bandwidth of the system; however, if other factors such as the speed of a controller (e.g., a local microprocessor), rate of actuator control, and position sensing resolution already degrade the bandwidth, then such dampers may be acceptable. For example, inexpensive plastic dampers, such as rotational dampers produced by Fastex/Deltar, can be placed at desired bearing positions and have one end grounded. In other embodiments, this passive damping can be introduced by using the back electromotive force (EMF) of the actuators 54 to remove energy from the system. This can also be accomplished by using a shunt resistor coupled across the terminals of a motor or the coils of a voice coil actuator. Also, passive brakes, as mentioned above, can be used. In addition, in voice coil embodiments, multiple wire coils can be provided, where some of the coils can be used to provide back EMF and damping forces.

The transducers 51*a*–51*c* of the described embodiment are advantageously positioned to provide a minimal amount of inertia to the user handling object 12. All three of the transducers 51 are grounded meaning that each of the transducers is directly and rigidly coupled to ground member 34 which is coupled to ground surface 31, i.e., the ground surface carries the weight of the transducers, not the user handling object 12; and that none of the actuators must provide forces to overcome the carried weight of any of the other actuators. The weights and inertia of all the transducers 51 are thus substantially negligible to a user handling and moving object 12. This provides a more realistic interface to a virtual reality system, since the computer can control the transducers to provide substantially all of the forces felt by the user in these degrees of motion. In addition, the transducers 51*a*–51*c* are "decoupled," meaning that the actuators are decoupled in force such that force generated from one actuator does not impose forces (such as back drive forces) on any of the other actuators that must be compensated for. The motors/cables of the capstan drive mechanisms (described with respect to FIG. 6) are all tension independent, i.e., each motor and cable is substantially decoupled in tension from the other motors, thus allowing a more realistic and accurate force transmission system. In addition, the decoupling of the actuators allows the mathematical determination of forces providing a desired force sensation to the user object to be simpler and therefore faster than if the actuators were coupled.

Apparatus 14 is a high bandwidth force feedback system, meaning that the mechanical and electrical components allow high frequency signals to be used to control transducers 51 and these high frequency signals will be applied to the user object with high precision and dependability. The user feels very little compliance or "mushiness" when handling object 12 due to the high bandwidth. In contrast, in typical prior art arrangements of multi-degree of freedom interfaces, at least one actuator "rides" upon another actuator in a serial chain of links and actuators, or the user must carry the heavy weight of at least one actuator when manipulating object 12. This low bandwidth arrangement causes the user to feel the inertia of coupled actuators when manipulating an object. In addition, many prior art devices have coupled motors coupled together by cables, where the force applied by one motor creates tension on the other motors which must be compensated for and which leads to inaccurate force transmission and slow, complicated force calculations by the host computer. The present invention does not have to output compensating forces for the weight of any actuators, has tension-independent motors and cables; therefore, a full three degrees of freedom are actuated by grounded actuators with substantially no coupling, thus providing an accurate mechanical force feedback interface for 3-D virtual reality and simulation applications.

Floating gimbal mechanism 32 is included in the described embodiment of mechanical apparatus 14 to provide additional degrees of freedom to object 12. Gimbal mechanism 32 includes a first member 60 rigidly coupled to central member 38a of linkage 30, and a second member 62 pivotally coupled to the first member 60. Object 12 is rigidly coupled to second member 62. Gimbal mechanism 32 provides two additional degrees of freedom (i.e., fourth and fifth degrees of freedom) to object 12: a rotary degree of freedom about axis G, and a different rotary degree of freedom about axis H that is substantially perpendicular to axis G. Gimbal mechanism 32 preferably includes sensors to track the position of user object 12 in the fourth and fifth degrees of freedom provided by the gimbal mechanism about axes G and H. In preferred embodiments, a sixth degree of freedom is provided as a rotary "spin" movement of the stylus 35 about an axis I extending through member 38a. In such an embodiment, a sensing mechanism 64 can be included to track the motion about axis I, described with reference to FIG. 8b. The gimbal mechanism 32 preferably includes capstan drive mechanisms and is described in greater detail with respect to FIG. 8. Alternatively, the object 12 can be rotated and sensed in a sixth degree of freedom about its own lengthwise axis I'. In yet other embodiments of mechanical apparatus 14, gimbal mechanism 32 can be omitted and user object 12 can be coupled directly to linkage 30.

User manipulatable object (or "user object") 12 is coupled to mechanical interface 14 and is preferably an interface object for a user to grasp, grip, or otherwise manipulate in three dimensional (3D) space. User object 12 may be moved in all provided five degrees of freedom provided by linkage 30 and gimbal mechanism 32 and additional degrees of freedom if implemented. One example of a user object 12 is a stylus 35 as shown in FIG. 2, which can be grasped and manipulated by the user to point to various positions in 3-D space at various orientations. By "grasp," it is meant that users may releasably engage a portion of the object in some fashion, such as by hand, with their fingertips, or even orally in the case of handicapped persons.

Stylus 35 can be used, for example, to control a computer-generated object in a virtual environment, such as a cursor, virtual stylus, pointer, or other object. The user can move the stylus in 3D space to point to graphical objects or write words, drawings, or other images, etc. displayed on a display device. A virtual stylus can be presented in a virtual hand of the user on the display device. The computer system tracks the position of the stylus with sensors as the user moves it. The computer system also provides force feedback to the stylus when the user moves the stylus against a generated surface such as a virtual desk top, writes on a virtual pad of paper, etc. It thus appears and feels to the user that the stylus is contacting a real surface. In addition, the stylus 35 can include additional controls, such as one or more buttons that initiate specific commands to computer system 18 when the user depresses the buttons. In yet other embodiments, other additional peripheral devices can be coupled to computer system 18 and/or mechanical apparatus 14 to operate in conjunction with stylus 35, such as a mouse, track ball, foot pedal, voice recognition hardware, etc.

In other embodiments, different user objects 12 can be coupled to linkage 30. An example of a medical instrument is described with reference to FIG. 5. Other medical instruments, joysticks, grips, etc., can be provided as user object 12 in other embodiments, as described above.

Optionally, additional transducers can be added to mechanical interface 14 in provided or additional degrees of freedom of object 12. For example, actuators can be added to gimbal mechanism 32 to provide forces in the fourth fifth and sixth degrees of freedom about axes G, H, and I. Such actuators would preferably be smaller than the actuators 54a–c, since the user would need to carry the weight of actuators on gimbal mechanism 32.

Figure 5:
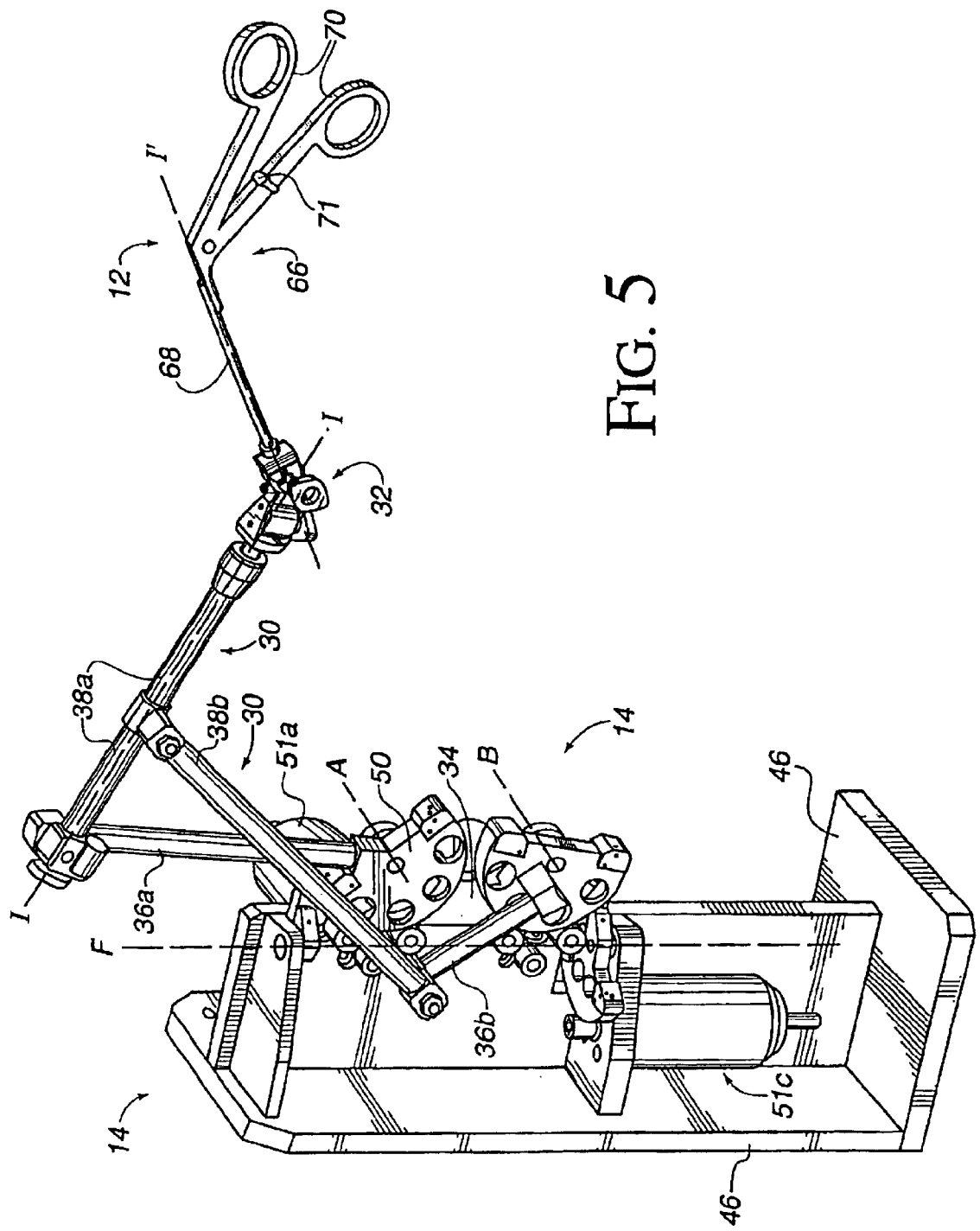
FIG. 5 is a perspective view of the mechanical apparatus of FIG. 2 having a medical instrument as a user manipulable object.

FIG. 5 is a perspective view of mechanical apparatus 14 having a medical instrument 66 for user object 12. Mechanical apparatus 14 shown in FIG. 5 operates substantially the same as the apparatus shown in FIGS. 2–4. User object 12, however, is a medical instrument 66 which the user can move in six degrees of freedom. In the described embodiment, medical instrument 66 are forceps, which can be used, for example, to perform surgery procedures in the skull of a patient by inserting a shaft through the nasal passages of the patient. A portion of the shaft 68 can be coupled to central member 38a of linkage 30. The grip portion 70 of the instrument 66 is grasped by the user as in a normal surgical procedure.

A medical procedure is simulated by sensing the motion of the medical instrument 66 and outputting forces on the instrument as appropriate. A user can move the medical instrument 66 in the six provided degrees of freedom, similar to the stylus 53 of FIG. 2. The movements in these six degrees of freedom will be sensed and tracked by computer system 18 using the sensors 52a–c, sensors included in gimbal mechanism 32 and the sensor of mechanism 64 (described below with reference to FIGS. 8 and 8b). Forces can be applied in the first three degrees of freedom by the computer system to simulate the instrument impacting a portion of the simulated subject body, experiencing resistance moving through body tissues, etc. In addition, a visual representation of the tool in the simulated tissues can be displayed on display screen 20 by computer 18 that is coordinated with the forces and motion of instrument 66. In this way, both the feel and appearance of a procedure of inserting instrument 66 into body cavities and tissue is realistically simulated to provide a trainee a useful training process. Thus, when a surface is generated on the computer screen, the computer will send feedback signals to the object 12 and mechanical apparatus 14 using actuators 54a–c for generating appropriate forces in response to the position of a virtual instrument relative to the surface depicted on the computer screen.

In the described embodiment, medical instrument 66 includes sensors and not actuators for the fourth through sixth degrees of freedom, similar to the embodiment of FIG. 2. Actuators can be provided for these degrees of freedom if desired. The sixth degree of freedom is preferably provided as "spin" about the axis I or axis I' through the instrument, and can be sensed with an additional sensor. For typical medical procedures, rotational force feedback to a user about axis I is typically not required to simulate actual operating conditions. In alternate embodiments, an actuator such as a motor can be included to provide force about axis I or axis I'.

In some embodiments, the movement of medical instrument 66 can be constrained such that a shaft portion 68 has only three or four free degrees of motion. For some medical instruments, this is a good simulation of the real use of a medical tool in that once it is inserted into a patient, it is limited to about four degrees of freedom. The shaft 68 can be constrained at some point of along its length such that it can move with four degrees of freedom within the patient's body.

Another example of a medical user object is a laparoscopic tool used to simulate a laparoscopic medical procedure. The virtual reality system 10 may include a barrier and a standard laparoscopic trocar. The barrier is used to represent portion of the skin covering the body of a patient, and the trocar is inserted into the body of the virtual patient to provide an entry and removal point from the body of the patient for the laparoscopic tool, and to allow the manipulation of the laparoscopic tool.

Additional transducers can also be added to the medical instrument 66. For example, a transducer 71, such as a Hall effect sensor, can be added to grip 70 of instrument 66 to sense when the user moves the two portions of the grip 70 relative to each other to simulate extending a cutting blade of the tool. Such sensors are described in U.S. Pat. No. 5,623,582, filed Jul. 14, 1994 and entitled "Method and Apparatus for Providing Mechanical I/O for Computer Systems" assigned to the assignee of the present invention and incorporated herein by reference in its entirety.

Figure 5A:
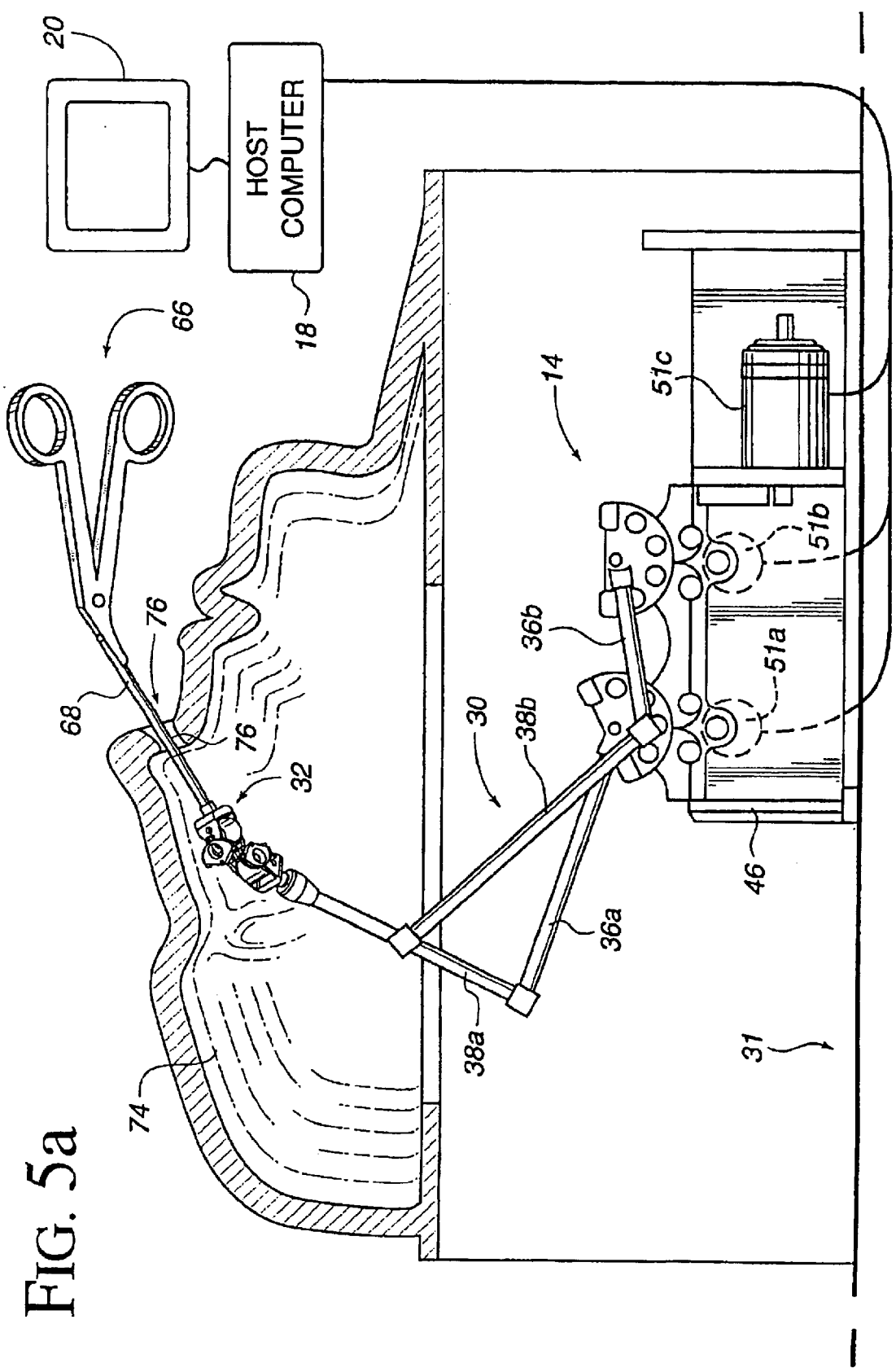
FIG. 5a is a diagram of a surgical simulator using the medical instrument and mechanical apparatus of FIG. 5.

FIG. 5a is a diagram illustrating one embodiment of using mechanical apparatus 14 with medical instrument 66 in a force feedback medical simulator 72. In the example shown, a simulation of an endoscopic nasal surgical procedure is provided, where foreceps 66 are inserted into a patient's nostrils, through a nasal passage, and into a simulated sinus cavity.

Simulator 72 includes mechanical apparatus 14, foreceps 66, shaft 68, and a head model 74. Mechanical apparatus 14 is provided behind head model 74 so that it cannot be seen by the trainee/user of the simulator. Head model 74 can be made of rubber, plastic, or other resilient material. The actuators of the mechanical apparatus 14 are coupled to a ground surface 31. Shaft 68 is coupled to floating gimbal mechanism 32 in the place of stylus 35 of FIG. 2. Shaft 68 of foreceps 66 extends from the floating gimbal mechanism and out through an orifice 76 in head model 74, the orifice representing a patient's nostril. The forceps 66 can be pivoted about its shaft 68 at an entry point located at the orifice 76. The nostril can thus be used as a constraint to movement, similar to a trochar, to guide and angle the tool 66. In other embodiments, the orifice 76 can be provided with the use of a trochar or other tool, as is well known in the medical arts. Computer 18 monitors the position of the foreceps in the provided six degrees of freedom and controls the three dimensional forces on the foreceps using actuators 52a–c, as described with reference to FIG. 9.

In operation, the trainee/user handles the grip 70 of the forceps 66 and moves the foreceps 66 through the nasal passage in the provided six degrees of freedom. The head model 74 is useful in that the trainee can place his or her hands on the model to orient himself or herself as if he or she were performing the procedure on a real patient. Forces are exerted in three dimensions using the actuators of the mechanical apparatus 14 to simulate the walls of the nasal passage and the feel of other tissues. The user does not feel the weight of any of the actuators while manipulating the instrument. The trainee can thus receive an accurate surgical experience which can help the trainee perform the complex surgical tasks on a real patient. Additional tools can also be used in the surgical procedure; for example, a scope or other visual instrument can be inserted in the other nostril of head 74 to simulate providing a view of the nasal cavity. The view can be simulated by displaying simulated images of the nasal cavity on display screen 20 of computer 18.

Figure 6:
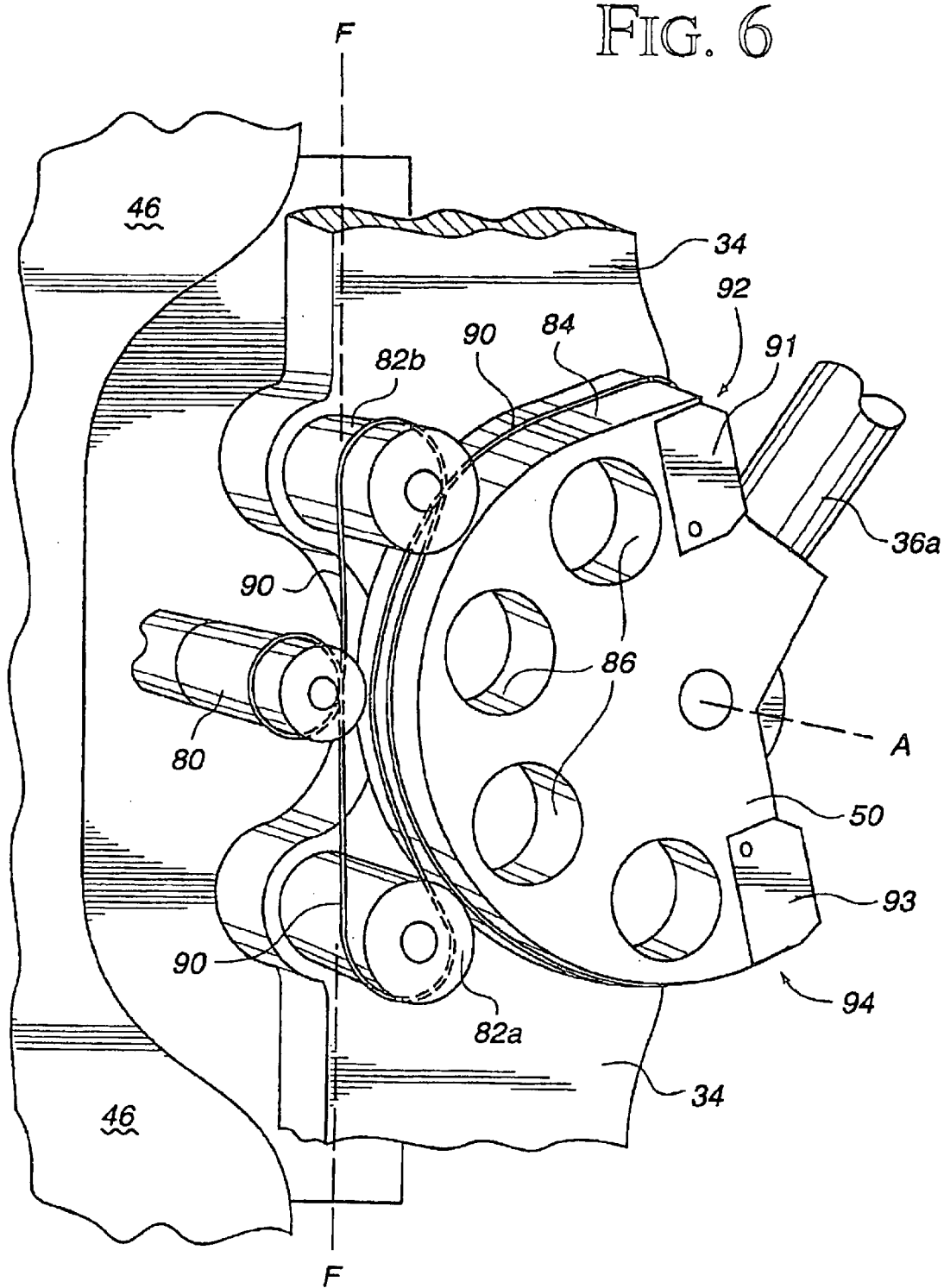
FIG. 6 is a detailed view of a capstan drive mechanism used for two degrees of freedom in the present invention.

FIG. 6 is a detailed view of capstan drive mechanisms 48a and 48b. The capstan drive mechanism 48a coupled to base member 36a is shown in FIG. 6; capstan mechanism 48b coupled to extension arm 36b is substantially similar to the mechanism presented here. Capstan drive mechanisms 48a and 48b include a capstan drum 50, capstan drive pulley 80, and capstan idler pulleys 82. Capstan drum 50 is a member having a spherical outer surface 84. In the described embodiment, drum 50 is an approximately semi-circular-shaped member. Apertures 86 are provided in drum 50 to reduce the weight of the drum and to thus allow the actuators to move the drum more easily. Alternatively, a single large aperture that extends between the edges of drum 50 can be provided to reduce the weight of the drum further, as described in U.S. Pat. No. 5,731,804 filed Jan. 18, 1995, assigned to the same assignee as the present application, and incorporated by reference herein in its entirety. Other shapes of drum 50 can be used in other embodiments. Drum 50 is rotatably coupled to carriage 46 so that the drum is rotatable about axis A (or axis B for capstan drive mechanism 48b). Base member 36a is rigidly coupled to drum 50 such that when capstan drum 50 is rotated about axis A, extension member 36a is also rotated. Curved outer surface 84 is preferably formed in an arc centered about axis A.

Three pulleys are included in capstan drive mechanism 48a. Drive pulley 80 is a cylindrical roller coupled to a shaft that is coupled to transducer 51a, the transducer including actuator 54a and sensor 52a. Actuator 54a drives the shaft and pulley 80 when so controlled by the computer system 18. Similarly, sensor 52a detects rotational movement of pulley 80 by detecting rotational change of position of the shaft. Idler pulleys 82a and 82b are cylinders rotatably coupled to carriage 46 and preferably rotate freely.

Capstan drum 50 is coupled to pulleys 80, 82a, and 82b by a cable 90. Cable 90 is preferably a thin, durable metal cable. Other types of flexible cables, cords, wire, string, bands, etc. can be used as well. Cable 90 is attached at a first end 92 of drum 50 on one side of the drum by a fastener 91, and the cable is drawn tautly against the outer surface 84 of drum 50. Cable 90 is wrapped around idler pulley 82a one or more times and is then routed to drive pulley 80 as shown. After being wrapped around drive pulley one or more times, the cable 90 is routed to idler pulley 82b, where it is wrapped one or more times. Finally, cable 90 is again drawn tautly against the outer surface 84 of drum 50 toward second end 94 and the second end of cable 90 is firmly attached to the drum 50 near end 94 by fastener 93.

Cable 90 should be routed such that it is substantially aligned with axis F in the portion routed between idler pulley 82a and drive pulley 80 and between idler pulley 82b and drive pulley 80. This configuration permits the torsional flexibility of the cable 90 to be utilized to allow the drum 50 to be rotated about axis F with carriage 46 while drive pulley 80 remains fixed to ground. That is, the twist of the cable between the idler pulleys and the drive pulley enables drum 50 to be rotated on carriage 34 about axis F with respect to the pulley 80, which remains fixed with respect to axis F, without significantly affecting the tension force on drum 50. This is because the tensioned cable can be rigid along its axial dimension to provide the necessary force transmission between drum and pulley, and the cable can simultaneously be torsionally flexible for torsion around the axial dimension to allow the rotation of drum 50 about axis F. Of course, the cable is also flexible along it length to allow it to be bent or wrapped around pulleys and drum 50.

Drive pulley 80 transmits rotational force from transducer 51a to capstan drum 50 and transmits force/motion from capstan drum 50 to transducer 51a. Rotational force is applied from transducer 51a to pulley 80 when the actuator 54a of transducer 51a rotates its shaft coupled to drive pulley 80. Drive pulley 80, in turn, transmits the rotational force via cable 90 to idler pulleys 82a and 82b. Idler pulleys 82a and 82b guide cable 90 to drum 50 and the force is transmitted to capstan drum 50, thus forcing the drum to rotate in a direction about axis A. Base member 36a rotates with capstan drum 50, thus causing force within the planar workspace of object 12 provided by linkage 30. Note that pulleys 80, 82a, and 82b, capstan drum 50 and extension member 36a will only actually rotate from the actuator-applied force if the user is not applying the same amount or a greater amount of rotational force to object 12 in an opposite direction to cancel the rotational movement. In any event, the user will feel the rotational force generated on object 12 as force feedback.

Pulleys 80, 82a and 82b are not threaded in the described embodiment, since the tension between cable and pulley is high enough to provide adequate friction between pulley and cable. In alternate embodiments, threads or grooves can be provided on one or more of the pulleys to help guide cable 90 and to allow less tension in cable 90. For example, cable 90 can be wrapped around pulley 80 so that the cable is positioned between threads, i.e., the cable is guided by the threads. As pulley 80 is rotated by transducer 51 a or by the manipulations of the user, the portion of cable 90 wrapped around the pulley 80 travels closer to or further from the end of the pulley, depending on the direction that pulley 80 rotates.

The capstan drive mechanisms 48a and 48b provide mechanical advantage to apparatus 14 so that the force applied to the user object 12 can be increased in magnitude without using more power or larger actuators. The ratio of the diameter of drive pulley 80 to the diameter of capstan drum 50 (i.e. double the distance from axis A to the edge 84 of capstan drum 50) dictates the amount of mechanical advantage, similar to a gear system. In the described embodiment of FIG. 2, the ratio of drum to pulley is equal to 6:1, although other ratios can be used in other embodiments.

Similarly, when the user moves object 12 in the x-z plane, base member 36a rotates about axis B and rotates capstan drum 50. This movement causes cable 90 to move, which transmits the rotational force around idler pulleys 82a and 82b to drive pulley 80. Pulley 80 and the shaft of transducer 51a rotate from this movement, and the direction and magnitude of the movement is detected by the sensor 54a of transducer 51a. As described above with respect to the actuators, the capstan drive mechanism provides a mechanical advantage to amplify the sensor resolution by a ratio of diameters of drum 50 to pulley 80 (15:1 in the preferred embodiment). A similar actuation and sensing process occurs for rotation of drum 50 of the other capstan drive mechanism 48b.

The tension in cable 90 should be at a level so that negligible backlash or play occurs between capstan drum 50 and pulleys 80, 82a, and 82b. Preferably, the tension of cable 90 can be adjusted by pulling more (or less) cable length through end 92 and/or end 94 of drum 50. For example, adjustable fasteners 91 and 93 are be included on the ends of curved surface 84 to tighten cable 90. A stop (not shown) can also be provided in the rotational path of drum 50 or base member 36a to prevent capstan drum 50 from moving beyond a designated angular limit and to prevent damage to components of the mechanical apparatus 14 due to user movement and generated forces.

Capstan drive mechanism 48 is advantageously used in the present invention to provide the described transmission of forces and mechanical advantage between transducers 51a–b and object 12 without introducing substantial compliance, friction, or backlash to the system. A capstan drive provides increased stiffness, so that forces are transmitted with negligible stretch and compression of the components. The amount of friction is also reduced with a capstan drive mechanism so that substantially "noiseless" tactile signals can be provided to the user. In addition, the amount of backlash contributed by a capstan drive is also negligible. "Backlash" is the amount of play that occurs between two coupled rotating objects in a gear or pulley system. Two gears, belts, or other types of drive mechanisms could also be used in place of capstan drive mechanism 48 in alternate embodiments to transmit forces between transducer 51a and base member 36a. However, gears and the like typically introduce some backlash in the system. In addition, a user might be able to feel the interlocking and grinding of gear teeth during rotation of gears when manipulating object 12; the rotation in a capstan drive mechanism is much less noticeable.

Since each capstan mechanism 48 includes its own cable that is not connected to any other capstan mechanism, and since the twist of the cable about axis F does not significantly affect the tension force on drum 50, each of the three actuators 52a–c are decoupled. That is, the force applied by once actuator in one cable does not affect the tension in other cables or actuators.

Importantly, the cable capstan drive shown in FIG. 6 also allows three actuators to be grounded in the mechanical apparatus 14 of the present invention without including a complex and/or low bandwidth transmission system. Drive pulley 80 can be coupled to transducer 48a and grounded, while pulleys 82a and 82b and drum 50 are coupled to carriage 34 and are therefore rotatable about axis F and not grounded. Cable 90 allows this configuration, since the cable is torsionally flexible and permits the drum sections of the capstan drives 48a–b to be moved about axis F relative to the drive pulley, which is stationary with respect to axis F. Idler pulleys 82a and 82b are provided to support the tension of cable 90 for drum 50 when carriage 46 is rotated. When the carriage 34 is rotated about axis F, the cables of both capstan drive mechanisms 48a and 48b twist to allow this rotation. Thus, the rotatable carriage 34 allows the planar workspace of linkage 30 to be rotated about axis F. Cable 90 acts as a rigid structural member with respect to transmission of forces between the pulley and drum, but also acts as a flexible member allowing the capstan drum to move its axis of rotation with respect to the pulley. The result is a mechanical interface allowing three degrees of freedom to a manipulated object and three grounded, decoupled actuators to provide highly realistic, high bandwidth forces to the user object 12.

Figure 7:
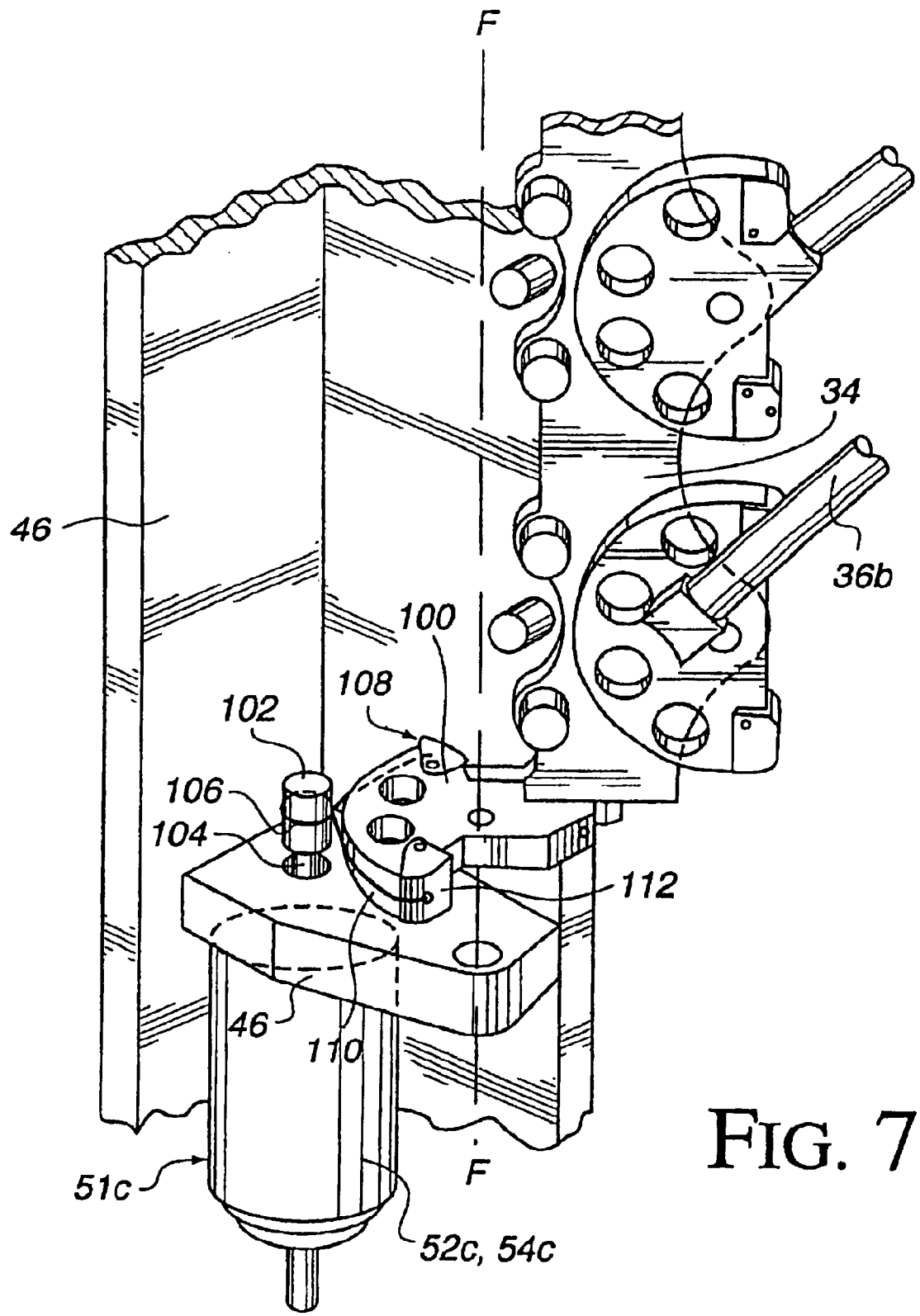
FIG. 7 is a detailed view of a capstan drive mechanism used for a third degree of freedom in the present invention.

FIG. 7 is a detail perspective view of capstan drive mechanism 48c. Drive mechanism 48c is similar to capstan drive mechanisms 48a and 48b, with the exception that no idler pulleys 82a and 82b are required in drive 48c since the axis of rotation of the drum 50 is not rotated with respect to the driven pulley, e.g., there is no rotation of the drum out of the plane defined by the pulley and drum.

Capstan drive mechanism 48c includes a capstan drum 100 and a pulley 102. Drum 100 is rigidly coupled to carriage 46 such that when carriage 46 is rotated about axis F, drum 100 is also rotated about axis F. Pulley 102 is rigidly coupled to a rotating shaft 104 of transducer 51c. Shaft 104 may be rotated by actuator 54c of transducer 51c, and sensor 52c of transducer 51c can detect rotational movement or position of shaft 104.

Capstan drum 100 is coupled to pulley 102 by a cable 106, similar to cable 90 of capstan drive mechanisms 48a and 48b. A first end of cable 90 is fastened to one end 108 of the curved surface 110 of drum 100. Cable 90 is drawn along surface 110 and is wrapped around pulley 102 one or more times as shown. Cable 90 is then drawn along the other portion of surface 110 to the second end 112 of the drum 100, where the second end of the cable is fastened as described above.

In operation, transducer 51c rotates shaft 104 and pulley 106, and cable 90 transmits the rotational force to drum 100. Drum 100 thus rotates about axis F, which causes the carriage 46 to rotate about axis F. Linkage 30, gimbal mechanism 32 and object 12 thus rotate about axis F since they are coupled to carriage 46. Likewise, when sensing motion, the user moves object 12 about axis F, which causes carriage 46 to rotate about axis F. This causes drum 50 to similarly rotate, and the rotational force is transmitted to pulley 102 through cable 106. The pulley 102 and shaft 104 rotate, and this rotation is sensed by sensor 52c.

Capstan drive mechanism 48c provides all the mechanical advantage, low backlash, and high bandwidth features discussed above for the other capstan drives. Since capstan drives 48a and 48b are coupled between ground member 34 and carriage 46 by flexible cables, the carriage can be moved in a third degree of freedom about axis F while maintaining actuator 54c at a grounded position, thereby increasing the accuracy of the forces transmitted to object 12 from transducer 51c and from object 12 to the transducer when object 12 is moved by the user.

FIG. 8 is detailed perspective view of floating gimbal mechanism 32 as shown in FIG. 2. In the preferred embodiments, the user object 12 is coupled to the gimbal mechanism 32 which provides two degrees of freedom to the user object in addition to the three degrees of freedom provided by linkage 30 and carriage 46 described above with reference to FIGS. 2 and 3.

Gimbal mechanism 32 includes a first gimbal member 110 and a second gimbal member 112. First member 110 is rigidly coupled to central member 38a at one end and is rotatably coupled to second member 112 at its other end. In the described embodiment, first member 110 is shaped in a "U" configuration having two legs such that an intermediate member 116 is rotatably coupled to the first member 110 between the legs of the "U." Intermediate member 116 is shown more clearly in FIG. 8a as a cross sectional view, where the member 116 is preferably shaped as a cross such that the legs of each "U" 110 and 112 are rotatably coupled on opposing legs of the cross.

First member 110 also preferably includes a capstan mechanism 118. A sensor 120 is preferably rigidly coupled between the legs of member 110 such that a rotatable shaft 122 of the sensor is coupled to a pulley 124 of capstan drive 118. Pulley 124 is coupled to a capstan drum 126 of the capstan mechanism 118 by a cable 128. The first end of cable 128 is fastened at one end 130 of drum 126 by a fastener 131 and is routed along surface 132 of the drum 126, around pulley 124, along surface 132, and to second end 134 of drum 126, where it is fastened by a fastener 135. Capstan drum 126 is rotatably coupled to member 110 and rigidly coupled to intermediate member 116 such that drum 126 and intermediate member 116 are rotatable about an axis G. Thus, when intermediate member 116 is rotated about axis G, drum 126 is also rotated. This causes cable 128 to move and pulley 124 to rotate. The rotation of pulley 124 causes rotation of shaft 122, and sensor 120 detects the position (or change in position) of the shaft and relays a signal to computer 18. Capstan mechanism 118 thus functions similarly to capstan drive 48c described with reference to FIG. 7. However, in the preferred embodiment, no actuator is coupled to shaft 122, since the gimbal mechanism is a floating, lightweight mechanism that has no grounded members.

Second member 112 is preferably a U-shaped member similar to first member 110 and is rotatably coupled to intermediate member 116. Second member 112 can rotate about axis G as intermediate member 116 rotates. Second member 112 includes a capstan mechanism 140 that is similar to capstan mechanism 118 of first member 110. Thus, a sensor 142 is rigidly coupled between legs of second member 112 such that a rotatable shaft 144 of the sensor is coupled to a pulley 146 of capstan mechanism 140. Pulley 146 is coupled to a capstan drum 148 of the capstan mechanism 140 by a cable 150. The first end of cable 150 is fastened at one end 152 of drum 148 by a fastener 153 and is routed along a surface 154 of the drum 148, around pulley 146, along surface 154, and to second end 156 of drum 148, where it is fastened by a fastener 157. Capstan drum 148 is rotatably coupled to member 112 and is rigidly coupled to intermediate member 116. Member 112 can be rotated about an axis H that is substantially perpendicular to axis G with respect to drum 148 and intermediate member 116. Thus, when second member 112 is rotated about axis H, drum 148 and intermediate member 116 do not rotate. This causes cable 150 to move and pulley 146 to rotate, thus causing rotation of shaft 144, which sensor 142 detects. The sensor 142 outputs an appropriate signal to computer 18.

Figure 8B:
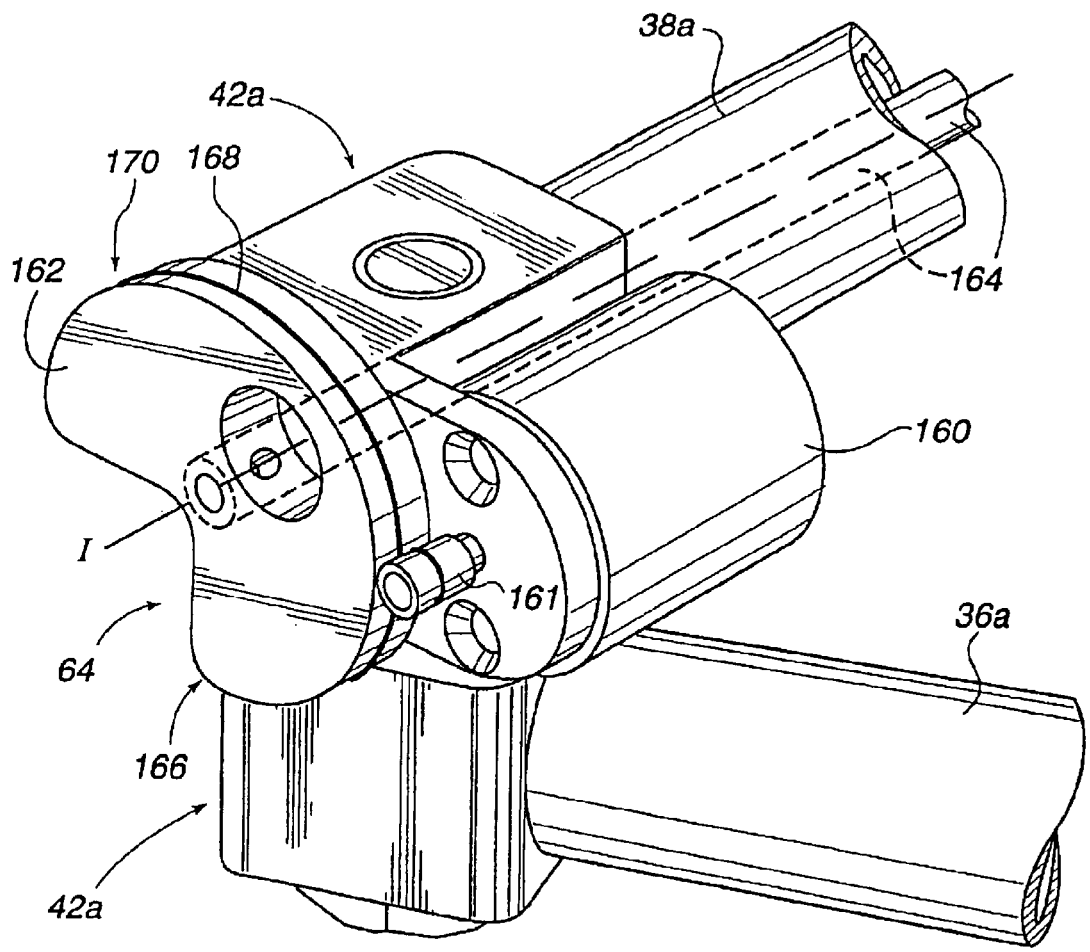
FIG. 8b is a perspective view of a capstan mechanism and sensor used for a sixth degree of freedom.

Stylus 35 or other user object 12 is rigidly coupled to second member 112. Thus, stylus can be moved about axis H in conjunction with second member 112. In addition, stylus 35 can be moved about axis G in conjunction with second member 112 and intermediate member 116. Object 12, such as stylus 35, is rotatably coupled to member 112 and can be spun about an axis I. A sensor is preferably included at the opposite end of member 38a to measure such movement, as shown in FIG. 8b. Alternatively, the sensor can be included at the near end of member 38a. In yet other embodiments, object 12 can be spun about axis I', and a sensor can be coupled between user object 12 and member 112 to sense this rotation for computer 18.

In the preferred embodiment, six degrees of freedom of user object 12 are sensed. Thus, both the position (x, y, z coordinates) and the orientation (roll, pitch, yaw) of the user object can be detected by computer 18 to provide a highly realistic simulation. In other embodiments, different mechanisms besides the floating gimbal mechanism 32 can be used to provide the fourth, fifth and sixth degrees of freedom; or fewer degrees of freedom can be provided.

The capstan mechanisms 118 and 140 provide mechanical reduction for the sensors 120 and 142, and thereby enhance the resolution of the sensors in detecting position of the user object. In the described embodiment, at least 4:1 mechanical reduction can be attained. This sensor resolution enhancement allows much smaller sensors to be used, thus significantly reducing the size and weight of the floating gimbal mechanism to achieve a more realistic and accurate force feedback interface.

Sensors 120 and 142 can optical encoders as described above or any type of sensor that provides electrical signals indicating movement about an axis to electronic interface 16. In other embodiments, actuators can be included in addition to the sensors to provide forces about axes G and H (and I, if applicable) upon command from computer system 18 or other controller. However, actuators are preferably not included for the fourth, fifth, and sixth degrees of freedom in the described embodiment, since actuators are typically heavier than sensors and, when positioned at the locations of sensors 120 and 142, would create more inertia in the system. In addition, the force feedback for the first three degrees of freedom provided by linkage 30 and carriage 46 allows impacts and resistance to be simulated, which is typically adequate in many virtual reality applications. Force feedback in the fourth, fifth, and sixth degrees of freedom would allow torques on user object 12 to be simulated as well, which may or may not be useful in a particular application.

FIG. 8*b* is a perspective view of a sensing mechanism 64 that detects motion (or velocity, acceleration, etc.) of object 12 in the sixth degree of freedom about axis I. Mechanism 64 is included at the end of member 38*a* opposite to the floating gimbal mechanism. Alternatively, mechanism 64 can be provided at the same end as gimbal mechanism 32.

Sensing mechanism 64 preferably includes a sensor 160 including a rotatable shaft or pulley 161, a capstan drum 162, an interior shaft 164. Shaft 164 is rigidly coupled to bearing 45 and member 110 at one end of member 38*a* and extends through the interior of member 38*a*. Capstan drum 162 is rigidly coupled to the opposite end of shaft 164. Capstan drum 162 is coupled to shaft 161 by a cable 168, where cable 168 is wrapped from one end 166 of drum 162, around shaft 161, and to the other end 170 of drum 162, similarly to the capstan mechanisms of gimbal mechanism 32. The housing of sensor 160 is rigidly coupled to bearing 42*a* and the shaft 161 may rotate with respect to the housing.

When member 110 of gimbal mechanism 32 is rotated, bearing 45 and interior shaft 164 are also rotated. This, in turn, rotates drum 162 and shaft 161 via cable 168. Sensor 160 is thus able to sense rotation about axis I and send output signals to computer 18. The drum 162 and pulley 161 provide mechanical reduction and enhanced sensing resolution to sensor 160 similarly to gimbal mechanism 162.

Alternatively, sensor 160 can be provided at the bearing 45 end of member 38*a*, and wires to the sensor can be routed through member 38*a*. For example, the sensor 160 can be rigidly coupled to member 38*a* and rotating shaft 161 of sensor 160 can be coupled to member 110 (or, the opposite configuration can be used, with the rotating shaft coupled to member 38*a*).

Figure 9:
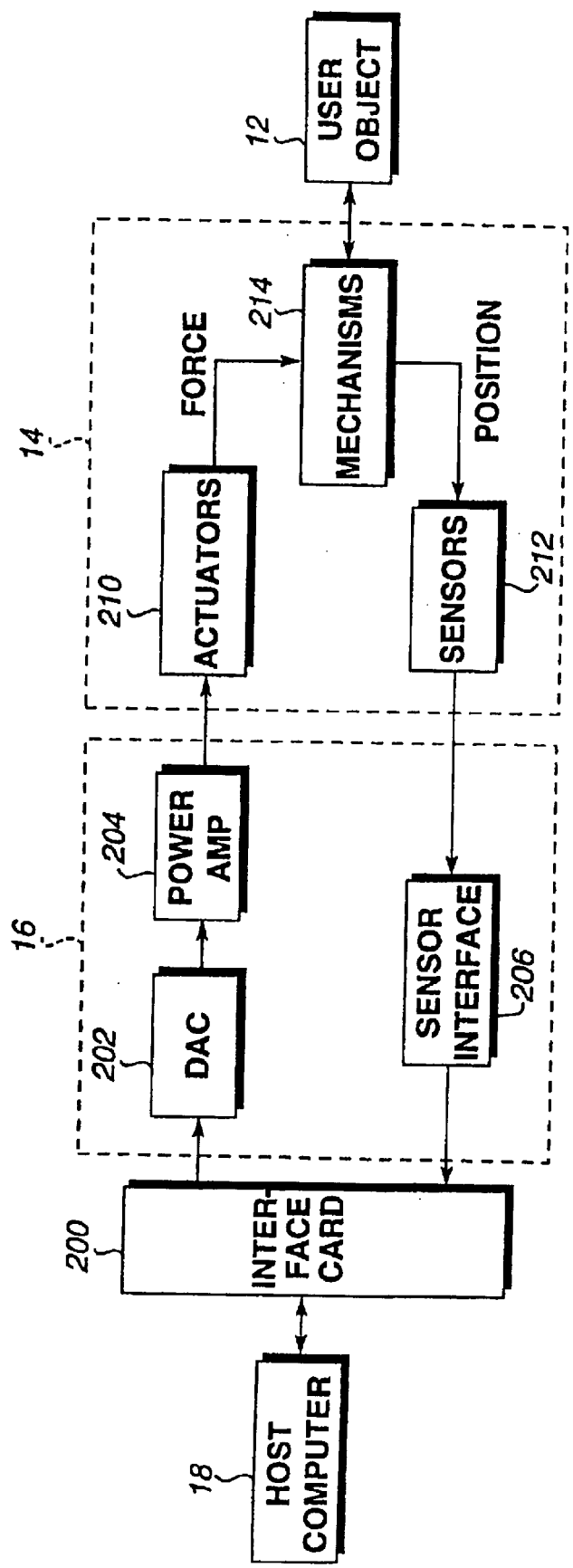
FIG. 9 is a block diagram of a computer and the interface between the computer and the mechanical apparatus of FIG. 2.

FIG. 9 is a block diagram of a computer 18 and an interface 16 to send and receive signals to and from mechanical apparatus 14. The interface 16 preferably includes such components as an interface card 200, DAC 202, power amplifier circuit 204, and sensor interface 206. In this embodiment, the interface 16 between computer 18 and mechanical apparatus 14 as shown in FIG. 1 can be considered functionally equivalent to the interface 16 enclosed within the dashed line in FIG. 9. Other types of interfaces 16 can also be used. For example, an electronic interface is described in U.S. Pat. No. 5,576,727, filed Jun. 5, 1995, assigned to the assignee of the present invention and incorporated herein by reference in its entirety. The electronic interface described therein has six channels corresponding to the six degrees of freedom of a mechanical linkage.

Interface card 200 is preferably a card which can fit into an interface slot of computer 18. For example, if computer 18 is an IBM AT compatible computer, interface card 16 can be implemented as an PCI, ISA, VESA, or other standard interface card which plugs into the motherboard of the computer, provides input and output ports connected to the main data bus of the computer, and may include memory, interface circuitry, and the like. In alternate embodiments, no interface card 200 need be used, and a direct interface bus can be provided from interface 16 and computer 18. For example, a serial interface such as RS-232, Universal Serial Bus (USB), or Firewire can be used to connect a serial port or parallel port of computer 18 to interface 16. Also, networking hardware and protocols, such as ethernet and TCP/IP, can also be used to communicate signals.

Digital to analog converter (DAC) 202 is coupled to interface card 200 and receives a digital signal from computer 18. DAC 202 converts the digital signal to analog voltages which are then sent to power amplifier circuit 204. DAC circuits suitable for use with the present invention are described in U.S. Pat. No. 5,731,804, incorporated by reference herein in its entirety. Power amplifier circuit 204 receives an analog low-power control voltage from DAC 202 and amplifies the voltage to control actuators of the mechanical apparatus 14. A suitable power amplifier circuit 204 is described in greater detail in U.S. Pat. No. 5,731,804. Sensor interface 206 receives and converts signals from sensors 52 to a form appropriate for computer 18, as described below.

Mechanical interface apparatus 14 is indicated by a dashed line in FIG. 9 and includes actuators 210, sensors 212, and mechanisms 214 including linkage 30, gimbal mechanism 32, and capstan drives 48. Actuators 210 can one or more of a variety of types of actuators, such as the DC motors 54, passive actuators, valves, or any additional actuators for providing force feedback to a user manipulated object 12 coupled to mechanical apparatus 14. The computer 18 determines appropriately scaled digital values to send to the actuators. Actuators 210 receive the computer signal as an amplified analog control signal from power amplifier 204.

Sensors 212 are preferably digital sensors that provide signals to computer 18 relating the position of the user object 12 in 3D space. In the preferred embodiments described above, sensors 212 are relative optical encoders, which are electro-optical devices that respond to a shaft's rotation by producing two phase-related signals and outputting those signals to sensor interface 206. In the described embodiment, sensor interface circuit 206 is preferably a single chip that converts the two signals from each sensor into another pair of clock signals, which drive a bi-directional binary counter. The output of the binary counter is received by computer 18 as a binary number representing the angular position of the encoded shaft. Such circuits, or equivalent circuits, are well known to those skilled in the art; for example, the Quadrature Chip from Hewlett Packard, California performs the functions described above.

Alternatively, analog sensors can be included instead of or in addition to digital sensors 212, such as potentiometers. Or, a strain gauge can be connected to the user object 12 to measure forces. Also, velocity sensors and/or accelerometers can be used to directly measure velocities and accelerations on object 12 in a particular degree of freedom. Analog sensors provide an analog signal representative of the position/velocity/acceleration of the user object in a particular degree of motion. In such an embodiment, sensor interface 206 includes an analog to digital converter (ADC) to convert the analog sensor signal to a digital signal that is received and interpreted by computer 18, as is well known to those skilled in the art.

Mechanisms 214 include linkage 30, floating gimbal mechanism 32, and capstan drives 48 and are operative to interface the movement and forces between the user object 12 and the sensors and actuators. From the mechanical movement of the mechanisms 214, the computer 18 receives inputs in the x-z plane from sensors 52a and 52b and inputs about axis F from sensor 52c; additional inputs about axes G, H and I are input from sensors 120, 142, and 160. Using the mechanical movement of the mechanisms 214, computer 18 outputs forces on the user object in the first three degrees of freedom.

Other input devices can also be included on user object 12 or on mechanical apparatus 14 to allow the user to input additional commands. For example, buttons, levers, dials, etc. can input signals to interface 16 to inform the computer 18 when these input devices have been activated by the user.

In other embodiments, the interface 16 can be included in computer 18 or in mechanical apparatus 14. In yet other embodiments, the interface 16 can include a separate, local microprocessor that is dedicated to handling much of the force feedback functionality of the mechanical apparatus 14 independently of computer 18. Such an embodiment, and other related interface functions, are described in greater detail with respect to U.S. Pat. No. 5,734,373, hereby incorporated by reference herein in its entirety.

While this invention has been described in terms of several preferred embodiments, it is contemplated that alterations, modifications and permutations thereof will become apparent to those skilled in the art upon a reading of the specification and study of the drawings. For example, the members of apparatus 14 can take a number of actual physical sizes and forms while maintaining the disclosed linkage structure. In addition, other gimbal mechanisms can also be provided included to provide additional degrees of freedom. Likewise, other types of gimbal or spatial mechanisms or different mechanisms providing multiple degrees of freedom can be used with the capstan drive mechanisms and grounded actuators disclosed herein to reduce inertia, friction, and backlash in a system. A variety of devices can also be used to sense the position of an object in the provided degrees of freedom and to drive the object along those degrees of freedom. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. An interface apparatus for interfacing motion of a user manipulable object with a computer system, said interface apparatus comprising:
   a user manipulable object being physically contacted by a user;
   a 3-D spatial mechanism coupled to said user object and including a plurality of members including a ground member coupled to a ground, said spatial mechanism providing at least three degrees of freedom to said user manipulable object with respect to said ground;
   three actuators rigidly coupled to said ground and coupled to said spatial mechanism, said actuators operative to apply forces in said three degrees of freedom to said user manipulable object in response to electrical signals from said computer system; and
   a sensor for detecting a position of said user manipulable object in three-dimensional space and for outputting sensor signals to said computer system.

2. An interface apparatus as recited in claim 1 wherein said three degrees of freedom include two degrees of freedom provided in a planar workspace and a third degree of freedom provided as rotation of said planar workspace about an axis, wherein a first and second of said actuators apply force in said planar workspace and a third of said actuators applies force about said axis.

3. An interface apparatus as recited in claim 2 wherein at least some of said plurality of members of said spatial mechanism are formed as a closed loop linkage that provides said planar workspace.

4. An interface apparatus as recited in claim 3 wherein said closed loop linkage includes five members, and wherein each of said five members of said closed loop linkage is rotatably coupled to at least two other members of said linkage, said five member linkage providing two of said three degrees of freedom.

5. An interface apparatus as recited in claim 1 wherein one of said members of said 3-D spatial mechanism is a rotatable carriage rotatably coupled to a ground member coupled to said ground, said carriage providing a third degree of freedom.

6. An interface apparatus as recited in claim 1 further comprising means for transmitting a force from one of said actuators to said spatial mechanism.

7. An interface apparatus as recited in claim 5 further comprising two capstan drive mechanisms, each coupled between one of said actuators and said closed loop linkage, wherein each of said capstan drive mechanisms includes a drum coupled to said carriage and a pulley coupled to one of said actuators, wherein a member of said linkage is coupled to said drum, and wherein said drum is coupled to said pully by a cable such that said actuator is operative to rotate said pulley and thereby transmit force to said linkage with no substantial backlash.

8. An interface apparatus as recited in claim 1 wherein said user manipulable object includes a stylus.

9. An interface apparatus as recited in claim 1 wherein said user manipulable object includes at least a portion of a medical instrument.

10. An interface apparatus as recited in claim 1 further comprising a floating gimbal mechanism coupling said one of said plurality of members to said user manipulatable object to provide rotational movement for said object in a fourth degree of freedom.

11. An interface apparatus as recited in claim 10 wherein said floating gimbal mechanism provides rotational movement for said user manipulable object in a fifth degree of freedom.

12. An interface apparatus as recited in claim 11 further comprising:
   a fourth degree of freedom transducer coupled between members of said floating gimbal mechanism; and
   a fifth degree of freedom transducer coupled between members of said floating gimbal mechanism.

13. An interface apparatus as recited in claim 11 wherein said user manipulable object is rotatable about a longitudinal sixth axis of said object to provide a sixth degree of freedom for said object, and further comprising a sixth degree of freedom transducer coupled between said object and said floating gimbal mechanism.

14. A method for interfacing motion of a user manipulable object with a computer system, said user manipulatable object being physically contacted by a user, said user manipulatable object being moveable in at least three degrees of freedom by use of a 3-D spatial mechanism coupled to said user manipulable object and including a plurality of members including a ground member rigidly coupled to a ground, said method comprising:

applying forces in three degrees of freedom to said user manipulable object in response to electrical signals from said computer system using three actuators rigidly coupled to said ground member of said spatial mechanism, said three actuators being decoupled in force from each other such that none of said actuators can apply a force to any of said other actuators; and detecting a position of said user manipulable object in three-dimensional space and outputting sensor signals to said computer system.

15. A method as recited in claim 14 wherein said actuators provide forces in said three degrees of freedom using tensioned cables, wherein tension in each of said cables is independent of a tension in said other cables.

16. A method as recited in claim 15 further comprising transmitting force to said linkage with no substantial backlash using two capstan drive mechanisms, each coupled between one of said first and second actuators and said plurality of members, wherein each of said capstan drive mechanisms includes a drum coupled to one of said members and a pulley coupled to one of said actuators, wherein a member of said linkage is coupled to said drum, and wherein said drum is coupled to said pully.

17. A method as recited in claim 14 wherein said three degrees of freedom include two degrees of freedom provided in a planar workspace and a third degree of freedom provided as rotation of said planar workspace about an axis with respect to said ground member.

18. A method as recited in claim 17 wherein sad two of said degrees of freedom are in a planar workspace provided by a parallel link mechanism, and a third of said degrees of freedom is provided by rotating said parallel link mechanism about an axis with respect to said ground member.

19. A mechanism for providing computer-controlled forces on a user manipulable object, the mechanism comprising:

a user manipulable object graspable by a user;

means for outputting a force in a degree of freedom of said user manipulatable object;

transmission means for transmitting force between said user manipulable object and said actuator, said transmission means including capstan drum means coupled to said user manipulable object and rotatable about a first axis and rotatable pulley means coupled to and rotatable by said means for providing a force, wherein a flexible member is coupled between said drum means and said pulley means to transmit rotational force between said drum means and said pulley means; and carriage means for rotating said user manipulatable object with respect to said ground surface about a second axis, wherein said drum means is rotatably coupled to said carriage means, and wherein said capstan drum means and said user manipulable object may be rotated about said second axis while said mean for outputting a force and said pulley means are fixed to said ground surface and do not rotate about said second axis, wherein said flexible member is twisted from said rotation about said second axis;

whereby said user manipulable object is provided with a first degree of freedom about said first axis and a second degree of freedom about said second axis.

20. A mechanism as recited in claim 19 further comprising a plurality of sensing means coupled to said mechanism, said sensing means for sensing a position of said user manipulatable object in said first and second degrees of freedom.

21. A mechanism as recited in claim 19 further comprising linkage means coupled between said user manipulatable object and said drum.

22. A mechanism as recited in claim 21 further comprising second transmission means, said second capstan transmission means including:

a second drum means coupled between said user manipulable object and said carriage means and rotatable about a third axis to allow said user manipulable object to be moved in a planar workspace having said first degree of freedom and a third degree of freedom;

second means for outputting a force coupled to said ground surface and being controllable to provide a force in said third degree of freedom of said user manipulable object; and second pulley means coupled to said second actuator and being coupled to said second capstan drum by a second flexible member.

23. A mechanism as recited in claim 22 further comprising a third means for outputting a force coupled to said ground surface, said third means outputting a force in said second degree of freedom, wherein said three means for outputting a force are each coupled to said ground surface.

24. A mechanism as recited in claim 23 further comprising a third transmission means coupled between said carriage and said third means for outputting a force, said third transmission means including third drum means rigidly coupled to said carriage means and rotatably coupled to said ground surface, third pulley means coupled to said third means for outputting a force, and a third flexible member coupled between said third drum means and said third pulley means.

25. A mechanism as recited in claim 24 wherein said flexible members are metal cables.

26. A mechanism as recited in claim 19 wherein said user manipulable object is one of a stylus and a medical instrument.

27. A mechanism as recited in claim 21 wherein said user manipulable object is coupled to said linkage means by floating gimbal means for providing at least two additional degrees of freedom to said user manipulable object.

28. An interface apparatus as recited in claim 27 wherein said floating gimbal mechanism includes at least one capstan drive mechanism and at least one sensor, said capstan drive mechanism providing enhanced sensing resolution to said sensor.

29. An interface apparatus for interfacing the motion of a stylus with a computer system that provides simulated feel sensations to a user holding said stylus, said interface apparatus comprising:

a stylus manipulatable by a user in at least three degrees of freedom with respect to a ground surface;

three actuators rigidly coupled to said ground surface;

a mechanism that couples said stylus to said three grounded actuators, said mechanism allowing motion of said stylus in said three degrees of freedom and transmitting forces from said actuators to said stylus in said three degrees of freedom, wherein said mechanism includes a plurality of rigid members and a plurality of flexible members, wherein flex of at least one of said flexible members enables motion of said stylus with respect to said ground surface; and at least one sensor that detects a position of said user manipulatable object in three dimensions with respect to said ground surface.

30. An interface apparatus as recited in claim 29 wherein said flex of said flexible member is an axial twist.

31. An interface apparatus as recited in claim 30 wherein said flexible members are cables.

32. An interface apparatus as recited in claim 29 wherein a plurality of members of said mechanism form a closed loop linkage of five rigid members, said closed loop linkage being driven by two of said three grounded actuators.

33. An interface apparatus as recited in claim 29 wherein said three degrees of freedom are translational degrees of freedom.

34. An interface apparatus as recited in claim 29 wherein said mechanism further comprises means for allowing three additional degrees of freedom of said stylus, said three additional degrees of freedom being rotational degrees of freedom, thereby allowing said stylus to be manipulated in a full six degrees of freedom with respect to said ground surface.

35. An interface apparatus as recited in claim 29 wherein two of said three actuators are oriented approximately parallel with respect to each other and said third of said three actuators is oriented approximately perpendicular to said two parallel actuators.

36. An interface apparatus as recited in claim 35 wherein said two parallel actuators drive rigid links that form a closed loop chain of five members to apply force upon said stylus in a two dimensional plane.

37. An interface apparatus as recited in claim 36 wherein said perpendicular actuator applies forces in at least one direction outside of said plane, thereby allowing forces in three dimensional space.

* * * * *